(12) United States Patent
Yanachkov et al.

(10) Patent No.: US 8,575,127 B2
(45) Date of Patent: Nov. 5, 2013

(54) ANTITHROMBOTIC DIADENOSINE TETRAPHOSPHATES AND RELATED ANALOGS

(75) Inventors: Ivan Borissov Yanachkov, Shrewsbury, MA (US); George Edward Wright, Worcester, MA (US)

(73) Assignee: GLSynthesis Inc., Worcester, MA (US)

( * ) Notice: Subject to any disclaimer, the term of this patent is extended or adjusted under 35 U.S.C. 154(b) by 176 days.

(21) Appl. No.: 13/128,356

(22) PCT Filed: Nov. 20, 2009

(86) PCT No.: PCT/US2009/006196
§ 371 (c)(1),
(2), (4) Date: Jul. 7, 2011

(87) PCT Pub. No.: WO2010/059215
PCT Pub. Date: May 27, 2010

(65) Prior Publication Data
US 2011/0257252 A1    Oct. 20, 2011

Related U.S. Application Data

(60) Provisional application No. 61/199,656, filed on Nov. 20, 2008.

(51) Int. Cl.
*A01N 43/04* (2006.01)
*A61K 31/70* (2006.01)
*C07H 19/20* (2006.01)
*C07H 19/04* (2006.01)

(52) U.S. Cl.
USPC ......... 514/47; 514/46; 536/26.13; 536/26.21; 536/26.22

(58) Field of Classification Search
None
See application file for complete search history.

(56) References Cited

U.S. PATENT DOCUMENTS

| | | | |
|---|---|---|---|
| 3,989,683 A | 11/1976 | Staba | |
| 5,049,550 A * | 9/1991 | Zamecnik | 514/47 |
| 5,635,160 A | 6/1997 | Stutts, III et al. | |
| 5,681,823 A | 10/1997 | Kim et al. | |
| 5,763,447 A | 6/1998 | Jacobus et al. | |
| 6,326,363 B1 | 12/2001 | Pohjala et al. | |
| 6,765,090 B2 | 7/2004 | Yerxa et al. | |
| 7,018,985 B1 * | 3/2006 | Boyer et al. | 514/48 |
| 7,132,408 B2 | 11/2006 | Boyer et al. | |
| 7,368,438 B2 | 5/2008 | Plourde, Jr. et al. | |
| 7,598,246 B2 | 10/2009 | Dixon et al. | |
| 8,288,545 B2 | 10/2012 | Yanachkov et al. | |
| 2005/0026864 A1 | 2/2005 | Dixon et al. | |

FOREIGN PATENT DOCUMENTS

| | | |
|---|---|---|
| WO | WO-2008/024169 A1 | 2/2008 |
| WO | WO-2010/056795 A1 | 5/2010 |

OTHER PUBLICATIONS

Blackburn et al., "$A_{p4}A$ and Other Dinucleoside Polyphosphates," McLennan, A.G. Ed. CRC Press: Boca Raton, FL, 305-342, 1992.
Blackburn et al. "Chemical Synthesis, Separation, and Identification of Diastereoisomers of P1,P4-Dithio-5',5'''-Diadenosyl P1,P4-Tetraphosphate and Its P1, P 3-Methylene Analogues," *Tetrahedron Lett.* 31, 4371-4374, 1990.
Chan et al., "P1,P4-Dithio-P2,P3-Monochloromethylene Diadenosine 5',5'''-P1,P4-Tetraphosphate: A Novel Antiplatelet Agent," *Proc. Natl. Acad. Sci. USA* 94:4034-4039, 1997.
Elzein et al., "2-Pyrazolyl-$N^6$-Substituted Adenosine Derivatives as High Affinity and Selective Adenosine $A_3$ Receptor Agonists," *J Med Chem.* 47:4766-4773 (2004).
Fischer et al., "2-Thioether 5'-O-(1-Thiotriphosphate)adenosine Derivatives as New Insulin Secretagogues Acting through P2Y-Receptors," J Med Chem. 42:3636-3646 (1999).
Goodman, "Chemical Syntheses and Transformations of Nucleosides," in *Basic Principles in Nucleic Acid Chemistry*, eds. Paul O. Ts'O and J. Eisinger, 1:94-208, 1974.
Guranowski, "Analogs of diadenosine tetraphosphate ($A_{p4}A$)," *Acta Biochim Pol.* 50(4):947-972 (2003).
Holler, The Chemistry of Dinucleoside Polyphosphates. *Ap4A and Other Dinucleoside Polyphosphates.* A. G. McLennan, 10-30 (1992).

(Continued)

*Primary Examiner* — Traviss C McIntosh, III
(74) *Attorney, Agent, or Firm* — Clark + Elbing LLP; Kristina Bieker-Brady

(57) ABSTRACT

The invention features compounds of formula I and methods of their use as antiplatelet and antithrombotic compounds: H/N=Qχ2OOOOΛQ2-N, HR6/NIf)(ˆXMO-MγτOM°τX1MQ')r(ˆrfHOOHHOOQHiNχiR2 Formula (I).

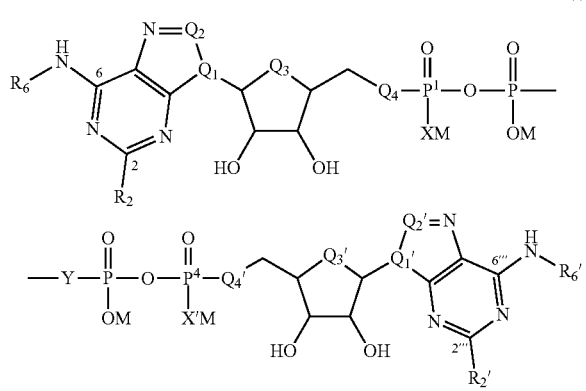

23 Claims, No Drawings

(56) References Cited

OTHER PUBLICATIONS

Ingall et al. "Antagonists of the Platelet $P2_{2T}$ Receptor: A Novel Approach to Antithrombotic Therapy," *J Med Chem.* 42:213-220 (1999).

Maeda et al., "Formation of ribonucleotide 2',3'-cyclic carbonates during conversion of ribonucleoside 5'-phosphates to diphosphates and triphosphates by the phosphorimidazolidate procedure," *Nucleic Acids Res.* 4:2843-2853, 1977.

McKenna et al., "Synthesis of α-Halogenated Methanediphosphonates," *Phosphorus and Sulfur and the Related Elements* 37:1-12, 1988.

Meisel et al., "Formation and ionization pattern of isoelectronic phosphorus compounds C1P(:O)2 and C1P(:S)2," CAS Accession No. 1990:36011, (1 page), 1989.

Murray and Atkinson, "Adenosine 5'-Phosphorothioate. A Nucleotide analog that is a substrate, competitive inhibitor, or regulator of some enzymes that interact with Adenosine 5'-Phosphate," *Biochemistry* 7:4023-4029 (1968).

Reiss and Moffatt, "Dismutation Reactions of Nucleoside Polyphosphates. III. The Synthesis of α,ω-Dinucleoside 5'-Polyphosphates," *J Org Chem.* 30:3381-3387, 1965.

Tarussova et al., "Organophosphorous analogs of biologically active compounds. XII Synthesis and properties of diadenosine tetraphosphate and its phosphonate analogs," *Bioorg. Khim.* 9(6):838-843 (1983).

Tarussova et al., "Phosphate and Halophosphonate Analogs of P1, P4-Bis(5'- Adenosyl)Tetraphosphonate and ATP," *Nucl Acids Res Symp Ser.* 14:287-288, 1984.

Véliz et al., "Substrate Analogues for an RNA-Editing Adenosine Deaminase: Mechanistic Investigation and Inhibitor Design," *J Am Chem Soc.* 125:10867-10876 (2003).

Vepsäläinen et al., "Bisphosphonic Compounds. Part 3. Preparation and Identification of Tetraalkyl Methylene- and (α-Halomethylene)bisphosphonates by Mass Spectrometry, NMR Spectroscopy and X-Ray Crystallography," *J Chem Soc Perkin Trans.* 2:835-842 (1992).

Wan et al., "A Highly Facile and Efficient One-Step Synthesis of $N^b$-Adenosine and $N^6$-2'-Deoxyadenosine Derivatives," *Org Lett.* 7:5877-5880 (2005).

Yanachkov et al., "P1,P2-diimidazolylderivatives of pyrophosphate and bis-phosphonates -synthesis, properties, and use in preparation of dinucleoside tetraphosphates and analogs," *Org Biomol Chem.* 9:730-738, 2011.

Yoshikawa et al., "A Novel Method for Phosphorylation of Nucleosides to 5'-Nucleotides," *Tetrahedr Lett.* 50:5065-5068 (1967).

Supplementary European Search Report and Annex to the European Search Report for European Patent Application No. 09827869, mailed May 7, 2012 (5 pages).

International Search Report for International Patent Application No. PCT/US09/06196, mailed Feb. 3, 2010 (8 pages).

\* cited by examiner

ANTITHROMBOTIC DIADENOSINE TETRAPHOSPHATES AND RELATED ANALOGS

CROSS-REFERENCE TO RELATED APPLICATIONS

This application is the national stage of International Application No. PCT/US2009/006196, filed Nov. 20, 2009, which claims benefit of U.S. Provisional Application No. 61/199,656, filed Nov. 20, 2008, which is hereby incorporated by reference.

FIELD OF THE INVENTION

This invention relates to symmetrical and asymmetrical $P^1,P^4$-diadenosine-tetraphosphates and related analogs.

BACKGROUND OF THE INVENTION

Platelets play critical roles in hemostasis and its pathophysiology. Undesired platelet activation is a result of many common pathologies, e.g., hypertension and arteriosclerosis, and leads to excessive platelet aggregation and the generation of occlusive thrombi (thrombosis). The ischemic events that follow, such as myocardial infarction and stroke, are leading causes of death in the developed world Antithrombotics are used in patients who are at increased risk of clotting, typically because of surgery, major trauma, vascular diseases, or blood clotting abnormalities. There are two major classes of antithrombotics: classical anticoagulants (e.g., heparin and warfarin), which interfere with the plasma clotting system, and antiplatelet drugs, which act by reducing the ability of platelets to aggregate. The anticoagulants are the preferred treatment of venous thrombosis, and antiplatelet drugs are preferred for arterial thrombosis. The two groups are less commonly used in combination, because of increased risk of major blood homeostasis compromise. The antiplatelet drugs have proven to be the safer group, especially for prophylactic and long term use.

The most popular group of antiplatelet agents is the group of thienopyridines, which irreversibly inhibits the platelet P2Y12 receptor. The most successful of this group, clopidogrel (Plavix®), alone or in addition to aspirin, has proven to be safe and moderately effective in reducing the composite endpoint of death from cardiovascular causes, nonfatal myocardial infarction, or stroke in patients with coronary syndromes (Yusuf et al. N. Engl. J. Med. 2001, 345:494-502; Savi and Herbert Semin. Thromb. Hemost. 2005, 31:174-83). Notwithstanding its widespread use, clopidogrel has important drawbacks. It is a prodrug, which has to be metabolized by two separate cytochrome P450 enzymes in the liver to produce the active substance. This causes a delay of action and necessitates "preloading" patients before a procedure and also results in significant inter-patient activity variability due to variations in the P450 system and liver function. Limited response to clopidogrel, often referred to as "clopidogrel resistance," occurs in up to 20% of patients. The requirement for liver metabolism also increases the potential for drug-drug interactions. The active metabolite of clopidogrel irreversibly inhibits P2Y12 platelet receptors, and its antithrombotic activity persists long after administration of the drug. The prolonged effect can be problematic, for example when urgent surgery is required, because of an increased risk for bleeding.

In the search for fast acting and reversible antiplatelet agents the adenosine triphosphate (ATP) scaffold has been extensively modified, which led to the development of the drug candidate Cangrelor, which is presently in advanced clinical development. An orally available adenosine analog related to Cangrelor, AZD 6140, is also in late stage clinical trials.

Bis-adenosine tetraphosphate ($Ap_4A$), like ATP, possesses weak antiplatelet activity. Yet, very few $Ap_4A$ analogs have been prepared and studied as possible antiplatelet agents. Bis-adenosine $P^2,P^3$-methylene-, and halomethylenetetraphosphates, and bis-adenosine $P^1,P^4$-dithio-$P^2,P^3$-monochloromethylenetetraphosphate have been disclosed as antiplatelet and antithrombotic agents in U.S. Pat. No. 5,049,550, and U.S. Pat. No. 5,681,823, respectively, albeit with activity insufficient for clinical development. Thus, there is a need for new diadenosine tetraphosphates and related analogs.

SUMMARY OF THE INVENTION

The invention provides compounds of Formula (I)

Formula I

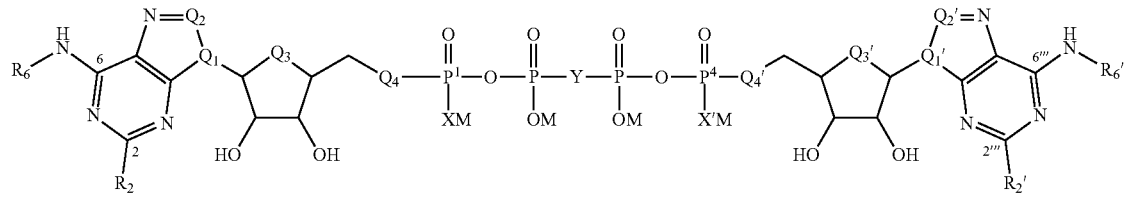

where $R_2$ and $R_2'$ are, independently, —H, —F, —Cl, —Br, —I, —R, —OR, —SR, —NHR, —OCOR, —SCOR, or —NHCOR; $R_6$ and $R_6'$ are, independently, —H, —R, or —COR, provided that $R_2$ and $R_6$ and $R_2'$ and $R_6'$ are not simultaneously H; $Q_1$, $Q_2$, $Q_1'$, and $Q_2'$ are independently N or CH; $Q_3$, $Q_4$, $Q_3'$, and $Q_4'$ are independently O or $CH_2$; X and X' are, independently, O or S; Y is O or CZZ', where Z and Z' are, independently, —H, —F, —Cl, —Br, —R, —OR, —SR, —NHR, —OCOR, —SCOR or —NHCOR; R is straight or branched chain alkyl (C1-C6), cyclic alkyl (C3-C6), straight or branched chain alkenyl (C2-C6), cyclic alkenyl (C4-C6), straight or branched chain alkynyl (C2-C6), cyclic alkynyl (C8-C10), aryl (C6-C12), heteroaryl (C2-C9), or heterocyclyl (C2-C9), wherein the alkyl, cyclic alkyl, alkenyl, cyclic alkenyl, alkynyl, cyclic alkynyl, aryl, heteroaryl, and heterocyclyl groups are substituted or unsubstituted; and each M is independently H or a pharmaceutically acceptable cation, wherein when two or more M are pharmaceutically acceptable cations, they may be combined to form a single pharmaceutically acceptable cation with the appropriate charge; or a pharmaceutically acceptable salt thereof or stereoisomer thereof. In certain embodiments, R is substituted or unsubstituted, straight or branched chain alkyl (C1-C6).

Examples include symmetrical and asymmetrical, base-substituted bis-$P^1,P^4$-diadenosinetetraphosphates, and their $P^1,P^4$-dithio, $P^2,P^3$-methylene, -halomethylene, and substituted methylene, and $P^1,P^4$-dithio-$P^2,P^3$-methylene, -halomethylene, and substituted methylene-tetraphosphonates. The compounds of the invention have antiplatelet activity in vitro and antithrombotic activity in vivo.

In certain embodiments, a compound of the invention has the formula Ia, II, or III or is a pharmaceutically acceptable salt thereof or stereoisomer thereof:

groups. In such embodiments, $P^1$ is in the $S_P$ or $R_P$ configuration, and $P^4$ may be in the same or the opposite configuration.

In other embodiments, X and X' are S, and Y is O, wherein $R_6$ is H, and $R_2$ is RS, where R is straight or branched chain alkyl (C1-C6), which is unsubstituted or substituted with one or more halogen atoms, aryl groups, heteroaryl groups, heterocyclyl groups, oxo groups, hydroxyl groups, alkoxy groups, aryloxy groups, alkylthio groups, arylthio groups, alkylamino groups, or aryl amino groups. In such embodiments, $P^1$ is in the $S_P$ or $R_P$ configuration, and $P^4$ may be in the same or the opposite configuration.

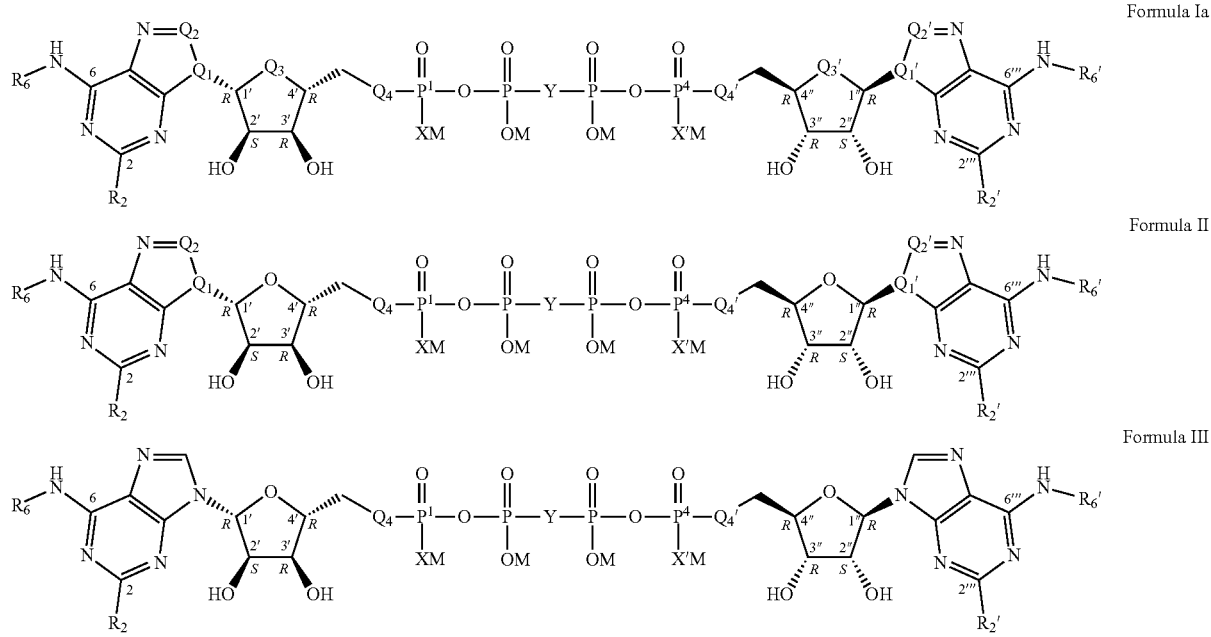

Formula Ia

Formula II

Formula III

In any of the above formulas, $R_2$ and $R_2'$ may be independently selected from —H, —Cl, —Br, —I, —SR, wherein R is substituted or unsubstituted, straight or branched chain alkyl (C1-C6). In any of the above formulas, $R_6$ and $R_6'$ may be independently selected from —H and substituted or unsubstituted straight or branched chain alkyl (C1-C6). Compounds of the invention may be symmetrical or asymmetrical.

In other embodiments, $R_2$ and $R_2'$ are, independently, —H, —F, —Cl, —Br, —I, —OR, —SR, —NHR, —OCOR, —SCOR, or —NHCOR, in which R is straight or branched chain alkyl (C1-C6), polyfluoroalkyl, or substituted alkyl (C2-C6); $R_6$ and $R_6'$ are, independently, —H, —R, or —COR, in which R is straight or branched chain alkyl (C1-C6), polyfluoroalkyl, or substituted alkyl (C2-C6); Y is O or $CZZ'$, where Z and Z' are, independently, —H, —F, —Cl, —Br, —R, —OR, —SR, —NHR, —OCOR, —SCOR, or —NHCOR, where R is straight or branched chain alkyl (C1-C6), polyfluoroalkyl, or substituted alkyl (C2-C6); $Q_1$ and $Q_1'$ are N; $Q_2$ and $Q_2'$ are CH; and $Q_3$, $Q_4$, $Q_3'$, and $Q_4'$ are O.

In other embodiments, X and X' are S, and Y is $CH_2$, CHCl, $CCl_2$, CHF, or $CF_2$, e.g., wherein $R_6$ is H, and $R_2$ is RS, where R is straight or branched chain alkyl (C1-C6), which is unsubstituted or substituted with one or more halogen atoms, aryl groups, heteroaryl groups, heterocyclyl groups, oxo groups, hydroxyl groups, alkoxy groups, aryloxy groups, alkylthio groups, arylthio groups, alkylamino groups, or aryl amino Specific examples of compounds of the invention are described herein.

The invention also features a pharmaceutical composition including a compound of the invention and a pharmaceutically acceptable excipient. Such compositions may be formulated for nasal inhalation.

The invention also features a method of inhibiting ADP-induced aggregation of human platelets in vitro by contacting human platelets with a compound of the invention in an amount sufficient to inhibit ADP-induced aggregation. The method is useful to prevent platelet aggregation in blood and blood products during storage. In certain embodiments, aggregation is inhibited by at least 10%, 20%, 30%, 40%, 50%, 60%, 75%, 85%, 90%, or 95% compared to aggregation in the absence of the compound.

The invention further provides a method of inhibiting aggregation of human platelets in vivo by administering an amount of a compound of the invention sufficient to inhibit platelet aggregation to a human in need thereof. In certain embodiments, aggregation is inhibited by at least 10%, 20%, 30%, 40%, 50%, 60%, 75%, 85%, 90%, or 95%.

The invention also provides a method of treating a human disease related to platelet aggregation by administering a therapeutically effective amount of a compound of the invention to a human in need thereof. Such diseases include venous thrombosis, thrombophlebitis, arterial embolism, coronary and cerebral arterial thrombosis associated with unstable angina, coronary angioplasty, or acute myocardial infarction, unstable angina, myocardial infarction, stroke, transient ischemic event, cerebral embolism, kidney embolism, pulmonary embolism, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, pathological effects of atherosclerosis and arteriosclerosis, chronic or acute states of hyper-aggregability, reocclusion of an artery or vein following fibrinolytic therapy, platelet adhesion associated with extracorporeal circulation, coronary artery disease, peripheral artery disease, and thrombotic complications associated with thrombolytic therapy.

The invention also features a method of treating arterial thrombosis, said method comprising administering, e.g., parenterally, a therapeutically effective amount of a compound of the invention to a human in need thereof.

By "alkyl" is meant a branched or unbranched saturated hydrocarbon group, desirably having from 1 to 6 carbon atoms. The term also includes monocyclic or bicyclic structures, in which each ring desirably has three to six members. Examples include methyl; ethyl; n-propyl; isopropyl; n-butyl; iso-butyl; sec-butyl; tert-butyl; pentyl; cyclopropyl; cyclobutyl; cyclopentyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; hexyl; and cyclohexyl. An alkyl group may be unsubstituted or substituted, as described herein.

By "alkenyl" is meant a branched or unbranched unsaturated hydrocarbon group having one or more carbon-carbon double bonds, desirably having from 2 to 6 carbon atoms. The term also includes monocyclic or bicyclic structures, in which each ring desirably has three to six members. Examples include ethenyl, 1-propenyl, 2-propenyl, 2-methyl-1-propenyl, 1-butenyl, 2-butenyl, and cyclohexenyl. An alkenyl group may be unsubstituted or substituted, as described herein.

By "alkynyl" is meant a branched or unbranched unsaturated hydrocarbon group having one or more carbon-carbon triple bonds, desirably having from 2 to 6 carbon atoms. The term also includes monocyclic or bicyclic structures, e.g., in which each ring has eight or more carbon atoms. Examples include ethynyl and 1-propynyl. An alkynyl group may be unsubstituted or substituted, as described herein.

By "aryl" is meant a monocyclic, bicyclic, or multicyclic carbocyclic ring system having one or more aromatic rings. Each ring preferably includes from 6-12 carbon atoms. Examples include phenyl, naphthyl, 1,2-dihydronaphthyl, 1,2,3,4-tetrahydronaphthyl, fluorenyl, indanyl, and indenyl. An aryl group may be unsubstituted or substituted, as described herein.

By "heteroaryl" is meant a monocyclic, bicyclic, or multicyclic heterocyclic ring system having one or more aromatic rings. Each ring preferably includes 2 to 9 carbon atoms and 1 to 4 oxygen, nitrogen, and/or sulfur atoms. Examples include benzimidazolyl, benzofuranyl, benzotriazolyl, furyl, imidazolyl, indolyl, isobezofuranyl, isoquinolinyl, isoxazolyl, oxazolyl, purinyl, pyrazinyl, pyridazinyl, pyridinyl, pyrimidinyl, pyrrolyl, quinolinyl, tetrazolyl, thienyl, triazinyl, and triazolyl. A heteroaryl group may be unsubstituted or substituted, as described herein.

By "heterocyclyl" is meant a monocyclic, bicyclic, or multicyclic heterocyclic ring system not including an aromatic ring. Each ring preferably includes 2 to 9 carbon atoms and 1 to 4 oxygen, nitrogen, and/or sulfur atoms. Examples include aziridinyl, morpholinyl, oxazolidinyl, oxazolinyl, oxecanyl, oxepanyl, oxiranyl, piperazinyl, piperidinyl, pyranyl, pyrrolidinyl, tetrahydrofuranyl, tetrahydropyranyl, tetrahydrothienyl, and tetrahydrothiopyranyl. A heterocyclyl group may be unsubstituted or substituted, as described herein.

By "halogen" is meant fluoro, bromo, chloro, or iodo.

By "alkoxy" is meant —OR, wherein R is an alkyl group.

By "aryloxy" is meant —OR, wherein R is an aryl group.

By "alkylthio" is meant —SR, wherein R is an alkyl group.

By "arylthio" is meant —SR, wherein R is an aryl group.

By "arylalkyl" is meant —RR', wherein R is an alkyl group, e.g., of 1 to 8 carbons, and R' is an aryl group, e.g., of 6 to 12 carbons.

By "fluoroalkyl" is meant an alkyl group substituted with one or more fluorine atoms.

By "perfluoroalkyl" is meant an alkyl group in which each hydrogen radical bound to the alkyl group has been replaced by a fluoride radical, such as trifluoromethyl.

By "alkylamino" is meant —NHR, wherein R is an alkyl group.

By "arylamino" is meant —NHR, wherein R is an aryl group.

By "disubstituted amino" is meant —NRR', wherein R and R' are independently alkyl, alkenyl, alkynyl, aryl, heteroaryl, and heterocyclyl.

By "quaternary amino" is meant —NRR'R"+, wherein R, R', and R" are independently alkyl, alkenyl, alkynyl, aryl, heteroaryl, and heterocyclyl.

By "aminoalkyl" is meant an alkyl group substituted with an amino, alkylamino, arylamino, disubstituted amino, or quaternary amino group.

By "hydroxyalkyl" is meant an alkyl group substituted with a hydroxyl group.

By "carboxyalkyl" is meant an alkyl group substituted with a carboxyl group.

By "oxo" is meant =O.

By "substituted" is meant that one or more hydrogen atoms of a group or portion of a group are replaced by substituents, including, but not limited to, $C_{1-6}$ alkoxy, $C_{6-12}$ aryloxy, sulfhydryl (—SH), $C_{1-6}$ alkylthio, $C_{6-12}$ arylthio, amino (—NH$_2$), disubstituted amino, quaternary amino, hydroxyl (—OH), carboxyl (—COOH), halogen, cyano (—CN), azido (—N$_3$), oxo, —C(O)—$C_{1-6}$ alkyl, —C(O)—$C_{6-12}$ aryl, —C(O)—$C_{5-12}$ heteroaryl, —C(O)—$C_{2-9}$ heterocyclyl, —(SO$_2$)—$C_{1-6}$ alkyl, —(SO$_2$)O—$C_{1-6}$ alkyl, —(SO$_2$)—$C_{6-12}$ aryl, —(SO$_2$)O—$C_{6-12}$ aryl, —(SO$_2$)—$C_{5-12}$ heteroaryl, —(SO$_2$)O—$C_{5-12}$ heteroaryl, —(SO$_2$)—$C_{2-9}$ heterocyclyl, and —(SO$_2$)O—$C_{2-9}$ heterocyclyl. In addition, alkyl, alkenyl, alkynyl, aryl, heteroaryl, and heterocyclyl groups may be substituted with $C_{6-12}$ aryl, $C_{4-12}$ heteroaryl (e.g., $C_{4-6}$ or $C_{5-12}$ heteroaryl), or $C_{2-12}$ heterocyclyl (e.g., $C_{2-9}$ or $C_{5-12}$ heterocyclyl) groups. Aryl, heteroaryl, and heterocyclyl groups may also be substituted with alkyl, alkenyl, or alkynyl groups, e.g., hydroxyalkyl, carboxyalkyl, fluoroalkyl, perfluoroalkyl, aminoalkyl, or $C_{7-20}$ arylalkyl. Substituents can in turn be substituted as described for the parent groups, e.g., with, halogen, trifluoromethyl, hydroxyl, or carboxyl.

By "pharmaceutically acceptable salts" are meant those derived from pharmaceutically acceptable inorganic and organic bases. For example, pharmaceutically acceptable salts are described in: Berge et al., *J. Pharmaceutical Sci-* ences 66:1-19, 1977 and in *Pharmaceutical Salts: Properties, Selection, and Use*, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like. Additional salts include nontoxic ammonium, quaternary ammonium, and amine cations, including, but not limited to, ammonium, tetramethylammonium, tetraethylammonium, methylamine, dimethylamine, trimethylamine, triethylamine, ethylamine and the like. Pharmaceutically acceptable cations are those salt-forming ions with a positive charge. References hereinafter to a compound according to the invention include compounds of the general formulae shown, as well as their pharmaceutically acceptable salts.

The term "pharmaceutical composition," as used herein, represents a composition containing a compound described herein, formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "prevent," as used herein, refers to prophylactic treatment or treatment that prevents one or more symptoms or conditions of a disease, disorder, or conditions described herein. Preventive treatment can be initiated, for example, prior to ("pre-exposure prophylaxis") or following ("post-exposure prophylaxis") an event that precedes the onset of the disease, disorder, or conditions. Preventive treatment that includes administration of a compound of the invention, or a pharmaceutical composition thereof, can be acute, short-term, or chronic. The doses administered may be varied during the course of preventive treatment. The term also includes prevention of activity in vitro, e.g., platelet aggregation.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term an "effective amount" or "sufficient amount" of a compound, as used herein, is that amount sufficient to effect beneficial or desired results, such as treatment or prevention, and, as such, an "effective amount" depends upon the context in which it is being applied.

The details of one or more embodiments of the invention are set forth in the accompanying description below. Other features, objects, and advantages of the invention will be apparent from the description and from the claims.

DETAILED DESCRIPTION

The invention provides compounds of the formula:

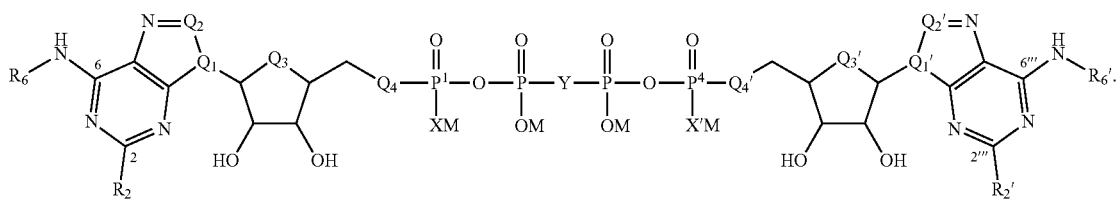

Examples include asymmetrical 2- and/or $N^6$-substituted-adenosine tetraphosphates and related $P^1,P^4$-dithio, $P^2,P^3$-methylene, -halomethylene, and substituted methylene, and $P^1,P^4$-dithio-$P^2,P^3$-methylene, -halomethylene, and substituted methylene-tetraphosphonates.

Specific compounds of the invention may also be of Formula Ia, II, or III.

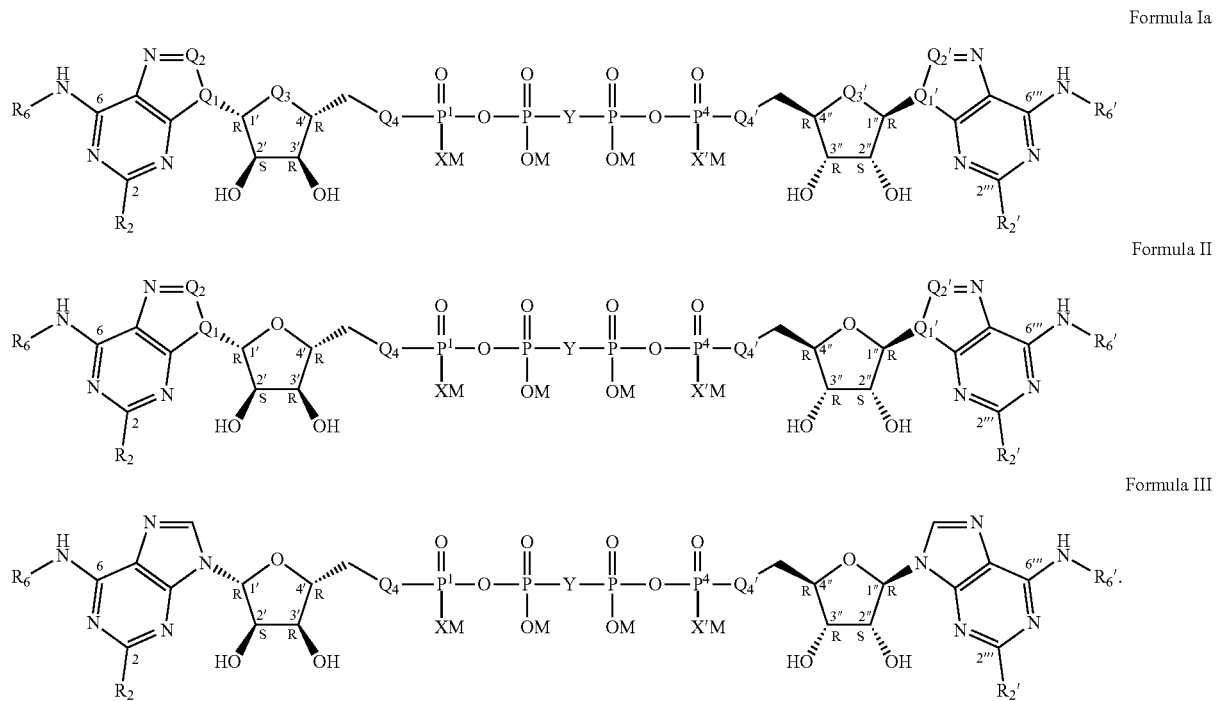

Formula Ia

Formula II

Formula III

The compounds of the invention may be used in the form of the free acid (or base) or in the form of salts.

The invention also includes all stereoisomeric forms of the compounds. For example, when X and/or X' is S, $P^1$ and/or $P^4$ may have the R or S configuration. In addition, when Y is CZZ', and Z and Z are not identical, Y may also be chiral, if the rest of the molecule is not symmetric. For compounds with X=X'=S, Y=O or CZZ' where Z and Z' are the same, four diastereomers with different stereo-configuration at $P^1$, and $P^4$ are possible, namely $R_{P1}R_{P4}$, $S_{P1}S_{P4}$, $R_{P1}S_{P4}$, and $S_{P1}R_{P4}$. If $R_2$=$R_2$', $R_6$=$R_6$', $Q_1$=$Q_1$', $Q_2$=$Q_2$', $Q_3$=$Q_3$', and $Q_4$=$Q_4$', a meso compound is formed, where the $R_{P1}S_{P4}$ and $S_{P1}R_{P4}$ configurations are equivalent. When $P^1$ and $P^4$ are in different absolute configuration, e.g., $S_{P1}R_{P4}$ or $R_{P1}S_{P4}$; Y=CZZ', and Z differs from Z', the carbon atom between $P^2$ and $P^3$ has two different phosphorous-containing substituents, may be chiral, and may contribute to the formation of additional stereoisomers (including meso forms when the molecule is otherwise symmetrical). Additional chiral centers are found in the carbon atoms of the five-membered ring containing $Q_3$ and its pendant 5' carbon and potentially in substituents at positions $R_2$, $R_2$', $R_6$, and/or $R_6$'. The individual diastereomers can be separated by analytical and preparative reverse phase HPLC as described by Blackburn and Guo (Tetrahedr. Lett., 1990, 31(30): 4371-4374) or by other methods for separations of stereoisomers known to the one of skill in the art. All such forms, including mixtures, are within the scope of the invention.

Specific examples of compounds of the invention are listed in Table 1.

TABLE 1

| Cpd No. | $R_2$ | $R_6$ | $R_2$' | $R_6$' | X | Y | X' | $Q_1$ and $Q_1$' | $Q_2$ and $Q_2$' | $Q_3$ and $Q_3$' | $Q_4$ and $Q_4$' | $P^1$ Config | $P^4$ Config |
|---|---|---|---|---|---|---|---|---|---|---|---|---|---|
| 1 | H | Me | H | Me | O | O | O | N | CH | O | O | — | — |
| 2 | SMe | H | SMe | H | O | O | O | N | CH | O | O | — | — |
| 3 | SMe | Me | H | H | O | O | O | N | CH | O | O | — | — |
| 4 | SMe | H | H | H | O | O | O | N | CH | O | O | — | — |
| 5 | SMe | H | H | Me | O | O | O | N | CH | O | O | — | — |
| 6 | SMe | Me | SMe | H | O | O | O | N | CH | O | O | — | — |
| 7 | SMe | Me | SMe | Me | O | O | O | N | CH | O | O | — | — |

TABLE 1-continued

| Cpd No. | R$_2$ | R$_6$ | R$_2$' | R$_6$' | X | Y | X' | Q$_1$ and Q$_1$' | Q$_2$ and Q$_2$' | Q$_3$ and Q$_3$' | Q$_4$ and Q$_4$' | P$^1$ Config | P$^4$ Config |
|---|---|---|---|---|---|---|---|---|---|---|---|---|---|
| 8 | H | Me | H | Me | S | CHCl | S | N | CH | O | O | R/S | R/S |
| 9 | SMe | H | SMe | H | O | CHCl | O | N | CH | O | O | — | — |
| 10 | SMe | H | SMe | H | S | O | S | N | CH | O | O | R/S | R/S |
| 11 | SMe | Me | H | H | S | O | S | N | CH | O | O | R/S | R/S |
| 12 | H | Pr | H | Pr | S | CHCl | S | N | CH | O | O | R/S | R/S |
| 13 | SMe | H | H | Me | S | O | S | N | CH | O | O | R/S | R/S |
| 14 | SMe | Me | SMe | H | S | O | S | N | CH | O | O | R/S | R/S |
| 15 | SMe | Me | SMe | Me | S | O | S | N | CH | O | O | R/S | R/S |
| 16 | H | Me | H | Me | S | CHCl | S | N | CH | O | O | R/S | R/S |
| 17 | SMe | H | SMe | H | S | CHCl | S | N | CH | O | O | R/S | R/S |
| 18 | SMe | Me | H | H | S | CHCl | S | N | CH | O | O | R/S | R/S |
| 19 | SMe | H | H | H | S | CHCl | S | N | CH | O | O | R/S | R/S |
| 20 | SMe | H | H | Me | S | CHCl | S | N | CH | O | O | R/S | R/S |
| 21 | SMe | Me | SMe | H | S | CHCl | S | N | CH | O | O | R/S | R/S |
| 22 | SMe | Me | SMe | Me | S | CHCl | S | N | CH | O | O | R/S | R/S |
| 23 | SEt | H | SEt | H | S | CHCl | S | N | CH | O | O | R/S | R/S |
| 24 | SEt | Me | SEt | Me | S | CHCl | S | N | CH | O | O | R/S | R/S |
| 25 | SEt | H | SEt | H | S | CCl$_2$ | S | N | CH | O | O | R/S | R/S |
| 26 | SPr | H | H | H | S | CHCl | S | N | CH | O | O | R/S | R/S |
| 27 | SPr | Me | H | H | S | CHCl | S | N | CH | O | O | R/S | R/S |
| 28 | SPr | H | SMe | H | S | CHCl | S | N | CH | O | O | R/S | R/S |
| 29 | SPr | H | H | Me | S | CHCl | S | N | CH | O | O | R/S | R/S |
| 30 | SPr | Me | SMe | H | S | CHCl | S | N | CH | O | O | R/S | R/S |
| 31 | SPr | Me | SMe | Me | S | CHCl | S | N | CH | O | O | R/S | R/S |
| 32 | SPr | H | SPr | H | S | CHCl | S | N | CH | O | O | R/S | R/S |
| 33 | SPr | Me | SPr | Me | S | CHCl | S | N | CH | O | O | R/S | R/S |
| 34 | CF$_3$CH$_2$CH$_2$S | H | CF$_3$CH$_2$CH$_2$S | H | S | CHCl | S | N | CH | O | O | R/S | R/S |
| 35 | CF$_3$CH$_2$CH$_2$S | Me | CF$_3$CH$_2$CH$_2$S | Me | S | CHCl | S | N | CH | O | O | R/S | R/S |
| 36 | CF$_3$CH$_2$CH$_2$S | H | CF$_3$CH$_2$CH$_2$S | H | S | CCl$_2$ | S | N | CH | O | O | R/S | R/S |
| 37 | n-C$_5$H$_{11}$S | H | n-C$_5$H$_{11}$S | H | S | CHCl | S | N | CH | O | O | R/S | R/S |
| 38 | n-C$_5$H$_{11}$S | Me | n-C$_5$H$_{11}$S | Me | S | CHCl | S | N | CH | O | O | R/S | R/S |
| 39 | n-C$_5$H$_{11}$S | H | n-C$_5$H$_{11}$S | H | S | CCl$_2$ | S | N | CH | O | O | R/S | R/S |
| 40 | I | H | I | H | S | CHCl | S | N | CH | O | O | R/S | R/S |
| 41 | I | H | I | H | S | O | S | N | CH | O | O | R/S | R/S |
| 42 | Br | H | Br | H | S | CHCl | S | N | CH | O | O | R/S | R/S |
| 43 | Br | H | Br | H | S | CCl$_2$ | S | N | CH | O | O | R/S | R/S |
| 44 | Cl | H | Cl | H | S | CHCl | S | N | CH | O | O | R/S | R/S |
| 45 | SMe | H | SMe | H | S | CCl$_2$ | S | N | CH | O | O | R/S | R/S |
| 46 | SMe | H | SMe | H | S | CCl$_2$ | O | N | CH | O | O | R/S | R/S |
| 47 | SMe | H | SMe | H | S | CCl$_2$ | S | CH | CH | O | O | R/S | R/S |
| 48 | SMe | H | SMe | H | S | CCl$_2$ | S | N | CH | CH | O | R/S | R/S |
| 49 | SMe | H | SMe | H | S | CCl$_2$ | S | N | CH | O | CH | R/S | R/S |
| 50 | SMe | H | SMe | H | S | CCl$_2$ | S | N | CH | CH | CH | R/S | R/S |
| 51 | SMe | H | SMe | H | S | CCl$_2$ | S | CH | CH | CH | CH | R/S | R/S |
| 52 | SMe | H | SMe | H | S | CCl$_2$ | S | N | N | O | O | R/S | R/S |
| 53 | SMe | H | SMe | H | S | CCl$_2$ | S | CH | N | O | O | R/S | R/S |
| 54 | SMe | H | SMe | H | S | CCl$_2$ | S | CH | N | CH | O | R/S | R/S |
| 55 | SMe | H | SMe | H | S | CCl$_2$ | S | CH | N | CH | O | R/S | R/S |
| 56 | SMe | H | SMe | H | S | CCl$_2$ | S | CH | N | CH | CH | R/S | R/S |
| 57 | SMe | H | SMe | H | S | CCl$_2$ | S | N | CH | O | O | R | R |
| 58 | SMe | H | SMe | H | S | CCl$_2$ | S | N | CH | O | O | R | S |
| 59 | SMe | H | SMe | H | S | CCl$_2$ | S | N | CH | O | O | S | S |

Compounds of the invention may be synthesized according to methods known in the art, with reference to examples provided herein. For example, methods for the synthesis of bis-nucleoside tetraphosphates are described in Holler "The Chemistry of Dinucleoside Polyphosphates" in *Ap4A and Other Dinucleoside Polyphosphates*; McLennan, A. G. Ed. CRC Press: Boca Raton, Fla., 1992, pp 9-30; Blackburn, et al. "Synthetic structural analogues of dinucleoside polyphosphates" in *Ap4A and Other Dinucleoside Polyphosphates*; McLennan, A. G. Ed. CRC Press: Boca Raton, Fla., 1992, pp 305-342; Blackburn and Guo Tetrahedron Lett. 1990, 31:4371-4374; Tarussova et al. Bioorg. Khim., 1983, 9:838-843; and International Publication No. WO 2008/024169. Methods for synthesis of nucleoside 5'-monophosphates and monothiophosphates are described in Yoshikawa et al. Tetrahedr. Lett. 1967, 50:5065-5068 and Murray and Atkinson Biochemistry 1968, 11:4023-4029. Additional information on various methods for synthesis of modified nucleotides and nucleosides is found in Pettit *Synthetic Nucleotides* Van Nostrand, 1972; Scheit *Nucleotide Analogs* Wiley, 1980; and Goodman "Chemical Synthesis and Transformation of Nucleosides" in Paul O. Ts'O, J. Eisinger (Ed.) *Basic Principles in Nucleic Acid Chemistry*, Vol. 1, 1974, pp 94-208.

Uses of the Compounds

The compounds of the invention may be employed for the inhibition of platelet aggregation, e.g., ADP-induced aggregation, in vitro or in vivo. Diseases and uses benefiting from the inhibition of platelet aggregation include thrombosis, such as venous thrombosis (deep vein thrombosis, veno-occlusive disease, and hematological conditions (thrombocythemia or polycythemia)), thrombophlebitis, arterial embolism, coronary and cerebral arterial thrombosis (associated with unstable angina, coronary angioplasty, and acute myocardial infarction), unstable angina, myocardial infarction, stroke, transient ischemic event, cerebral embolism, kidney embolisms, pulmonary embolisms, primary arterial thrombotic complications of atherosclerotic disease (thrombotic stroke, peripheral vascular disease, and myocardial infarction without thrombolysis), thrombotic complications of interventions of atherosclerotic disease (associated with angioplasty, percutaneous coronary intervention, endarterectomy (e.g., of the carotid artery), stent placement (e.g., in the carotid artery), and coronary or other vascular graft surgery), thrombotic complications of surgical or mechanical damage (tissue salvage following surgical or accidental trauma, reconstructive surgery including skin flaps, and reductive surgery), mechanically-induced platelet activation (cardiopulmonary bypass resulting in microthromboembolism), shunt occlusion (renal dialysis or plasmapheresis), thrombosis secondary to vascular damage and inflammation (vasculitis, arteritis, glomerulonephritis, or organ graft rejection), indications with a diffuse thrombotic/platelet consumption component (disseminated intravascular coagulation, thrombotic thrombocytopenic purpura, hemolytic uremic syndrome, heparin-induced thrombocytopenia, or pre-eclampsia/eclampsia), pathological effects of atherosclerosis and arteriosclerosis (arteriosclerosis, acute myocardial infarction, chronic stable angina, unstable angina, transient ischemic attacks, strokes, peripheral vascular disease, arterial thrombosis, preeclampsia, embolism, restenosis or abrupt closure following angioplasty, carotid endarterectomy, or anastomosis of vascular grafts), platelet aggregation and clot formation in blood and blood products during storage, chronic or acute states of hyper-aggregability (caused by DIC, septicemia, surgical or infectious shock, post-operative and post-partum trauma, cardiopulmonary bypass surgery, incompatible blood transfusion, abruptio placentae, thrombotic thrombocytopenic purpura, snake venom or immune diseases), reocclusion of an artery or vein following fibrinolytic therapy, platelet adhesion associated with extracorporeal circulation, coronary artery disease, peripheral artery disease, and thrombotic complications associated with thrombolytic therapy.

Pharmaceutical Compositions

The compounds of the invention may be formulated into pharmaceutical compositions for administration to human subjects in a biologically compatible form suitable for administration in vivo or in vitro. Accordingly, the present invention provides a pharmaceutical composition including a compound of the invention in admixture with a suitable diluent, carrier, or excipient.

In accordance with the methods of the invention, the described compounds or salts thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that it is easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 0.05 mg and 3000 mg (measured as the solid form). A preferred dose ranges between 0.05-500 mg/kg, more preferably between 0.5-50 mg/kg.

A compound of the invention can be used alone or in combination with other agents to treat, prevent, and/or reduce the risk of thrombosis or other disorders that benefit from inhibition of platelet aggregation. In combination treatments, the dosages of one or more of the compounds may be reduced from standard dosages when administered alone. In this case, dosages of the compounds when combined should provide a preventive or therapeutic effect.

In addition to the above-mentioned therapeutic uses, a compound of the invention can also be used in vitro, e.g., for the preservation or storage of blood products, and in diagnostic assays, screening assays, and as a research tool.

EXAMPLES

Example 1

Synthesis of Compound 2, tetrasodium $P^1,P^4$-bis-(2-methylthio-5'-adenosine)tetraphosphate Compound 2 was synthesized according to the following reaction scheme:

2-Thioadenosine (prepared as disclosed in U.S. Pat. No. 3,989,683) was S-methylated with 1.1 equivalents of methyl iodide in the presence of 1.2 equivalents of sodium hydride in anhydrous in N,N-dimethylformamide at room temperature (step a). 2-Methylthioadenosine was converted to 2-methylthioadenosine-5'-monophosphate (step b) by the method of Yoshikawa et al. (Tetrahedr. Lett. 1967, 6065-5068). The disodium salt of di-(1-imidazolyl)diphosphonic acid was prepared as disclosed in WO 2008/024169 from pyrophosphate and carbonyldiimidazole (steps c, and d).

Bis-triethylammonium salt of 2-methylthioadenosine-5'-monophosphate (179 mg, 0.30 mmol) was dissolved in anhydrous DMF (5 ml), and the solvent was evaporated under high vacuum (0.2 mm Hg) at 35° C. to produce a foam. The residue was dissolved in anhydrous DMF (5 ml) under nitrogen. Disodium salt of di-(1-imidazolyl)diphosphonic acid (32.2 mg, 0.1 mmol) was added to this solution, followed by anhydrous zinc chloride (408.9 mg, 3.0 mmol). The mixture was protected from moisture, stirred for 30 minutes, and then added to a stirred mixture of Chelex® 100 resin in the sodium form (10 ml, Sigma-Aldrich Corp. St. Louis, Mo.) and 0.1 M

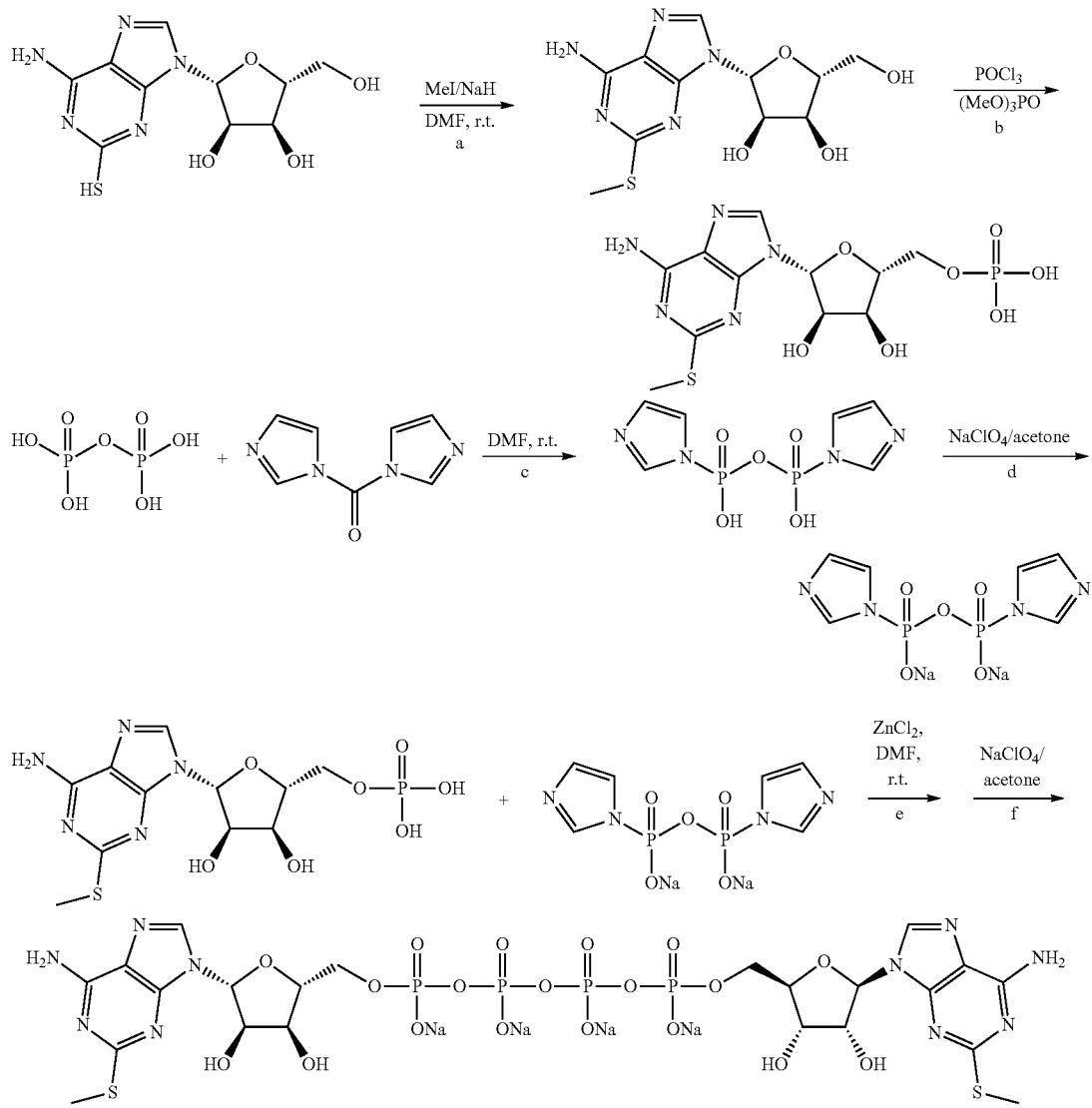

triethylammonium acetate buffer (20 ml, pH 8). After stirring for 15 minutes the mixture was filtered, and the resin was washed two times with water (10 ml each). The combined filtrate and washings were loaded on a column of QEA-Sephadex® (2.5×30 cm, Sigma-Aldrich Corp. St. Louis, Mo.) in the triethylammonium form, which was pre-equilibrated with 2 column volumes of 0.1 M triethylammonium bicarbonate buffer containing 10% (v/v) acetonitrile. A linear gradient of triethylammonium bicarbonate containing 10% (v/v) acetonitrile, from 0.1 to 1.5 M for 800 min, was passed through the column at a rate of 3 ml/min. The fractions containing the product were combined and evaporated under vacuum. The residue was re-evaporated three times from methanol (50 ml each), dissolved in methanol (0.5 ml) and mixed with a 2.0 M solution of sodium perchlorate in acetone (5 ml). The mixture was diluted with acetone (15 ml) and stirred for 2 hours. The white solid was collected by centrifugation, and washed by suspending in acetone (20 ml), centrifugation, and decanting. This acetone washing was repeated two more times, to give, after drying for 6 hours at high vacuum, 68.1 mg (67%) of compound 2. $^1$H NMR (300 MHz, D$_2$O) δ 8.15 (2H, s, H-8), 5.94 (2H, d, J=5.79 Hz, H-1'), 4.75-4.68 (2H, m, H-2'), 4.49 (2H, dd, J$_1$=3.9 Hz, J$_2$=4.8 Hz, H-3'), 4.32-4.26 (2H, m, H-4'), 4.23-4.17 (4H, m, H-5'), 2.46 (6H, s, SCH$_3$). $^{31}$P NMR ($^1$H dec., 121 MHz, D$_2$O), ppm: −11.01--11.36 (m, P$^1$+P$^4$), −22.45--22.81 (m, P$^2$+P$^3$). Electrospray MS in the negative ionization mode: Observed, 927.2 (100.0%), 928.1 (26.3%), 929.1 (15.9%), 930.1 (3.9%), 931.1 (0.9%); Calculated for [M-H]$^-$, C$_{22}$H$_{31}$N$_{10}$O$_{19}$P$_4$S$_2$—, m/e: 927.0 (100.0%), 928.0 (30.2%), 929.0 (17.4%), 930.0 (4.2%), 931.0 (1.2%).

Example 2

Synthesis of Compound 10, P$^1$,P$^4$-bis-(2-methylthio-5'-adenosine)-P$^1$,P$^4$-dithiotetraphosphate Compound 10 was prepared by the method in Example 1, steps e, and f, as the tetrasodium salt in 63% yield from 2-methylthioadenosine-5'-thiomonophosphate as the bis-triethylammonium salt. This compound is a mixture of 3 diastereomers with different stereo-configuration at P$^1$, and P$^4$, namely R$_{P1}$R$_{P4}$, S$_{P1}$ S$_{P4}$, and R$_{P1}$S$_{P4}$, which is equivalent to S$_{P1}$R$_{P4}$, and thus represents a meso-form. The individual diastereomers can be separated by analytical and preparative reverse phase HPLC as described by Blackburn and Guo (Tetrahedr. Lett., 1990 31(30):4371-4374). The ratio of the three diastereomers was determined by reverse phase HPLC to be 1:1:2. The characterization of compound 10 is as follows: $^1$H NMR (300 MHz, D$_2$O): δ 8.24 (0.5H, s, diast. 1H-8) 8.19 (0.5H, s, diast. 2H-8), 8.18 (1H, s, diast. 3H-8), 5.90 (2H, d, J=5.8 Hz, H-1'), 4.77-4.64 (2H, m, H-2'), 4.52-4.44 (2H, m, H-3'), 4.30-4.24 (2H, m, H-4'), 4.24-4.15 (4H, m, H-5'), 2.445 (3H, s, diast. 3 SCH$_3$), 2.435 (1.5H, s, diast. 1 or 2 SCH$_3$), 2.427 (1.5H, s, diast. 2 or 1SCH$_3$). $^{31}$P NMR ($^1$H dec., 121 MHz, D$_2$O), ppm: 43.53-42.94 (m, P$^1$-P$^4$), −23.93--24.39 (m, P$^2$+P$^3$).

2-Methylthioadenosine 5'-thiomonophosphate was made from 2-methylthioadenosine and phosphorous thiochloride in pyridine according to the method described by Fischer et al. (J. Med. Chem., 1999, 42:3636-3646) and was isolated in 60% yield as the bis-triethylammonium salt. All the other starting materials and intermediates were made as in Example 1.

Example 3

Synthesis of Compound 9, P$^1$,P$^4$-bis-(2-methylthio-5'-adenosine)-P$^2$,P$^3$-monochloromethylenetetraphosphate Compound 9 was prepared following Example 1, steps e, and f, from 2-methylthioadenosine 5'-monophosphate, which was prepared as in Example 1, and disodium chloromethylenebis-(1-imidazolylphosphinic acid), which was prepared as disclosed in WO 2008/024169 from monochloromethylene-bis-phosphonic acid, according to the scheme:

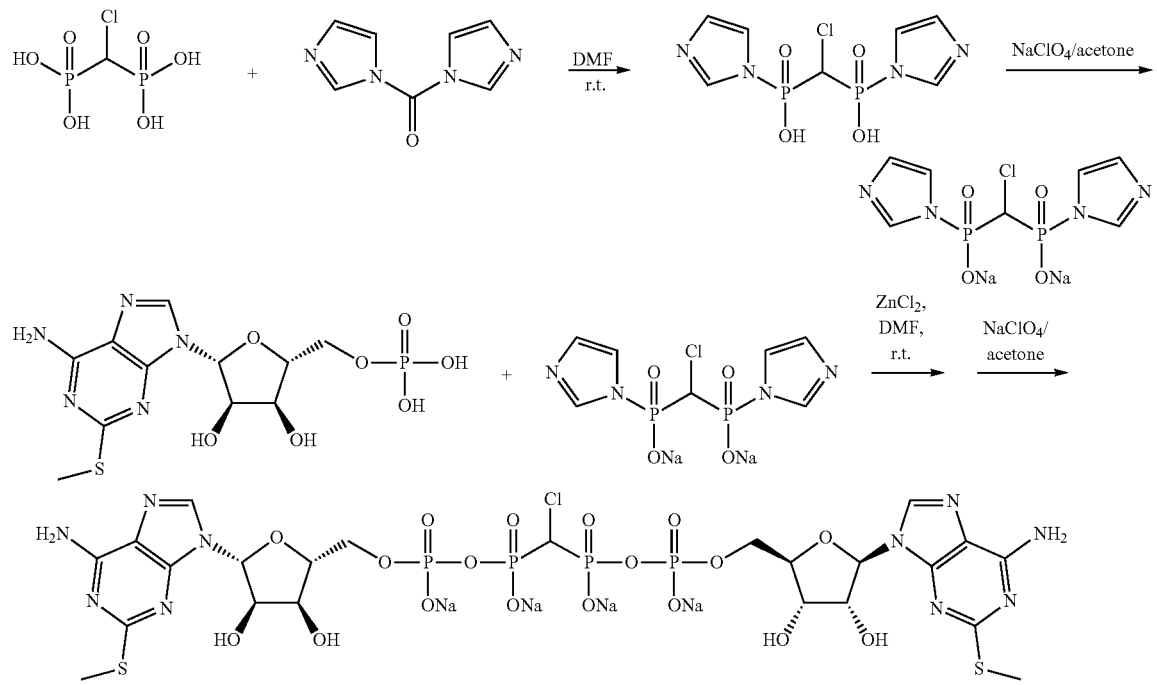

Monochloromethylene-bis-phosphonic acid was prepared from tetraethyl methylenediphosphonate, which was converted to tetraethyl dichloromethylenediphosphonate with sodium hypochloride as described by Vepsäläinen et al. (Journal of the Chemical Society, Perkin Transactions 1992, 2:835-842), then selectively reduced to tetraethyl monochloromethylene-bis-phosphonate with sodium sulfite and hydrolyzed to monochloromethylene-bis-phosphonic acid monopyridinium salt as described by McKenna et al. (Phosphorus sulfur and silicon and the related elements, 1988, 37:1-12).

Compound 9 was isolated as the tetrasodium salt in 79% yield. $^1$H NMR (300 MHz, D$_2$O): δ 8.14, 8.12 (2H, s, H-8), 5.95 (2H, d, J=5.5 Hz, H-1'), 4.73-4.67 (2H, m, H-2'), 4.51-4.47 (2H, m, H-3'), 4.28-4.23 (2H, m, H-4'), 4.18 (1H, t, $^2J_{P-H}$=15.0 Hz, CHCl), 4.21-4.09 (4H, m, H-5'), 2.449, 2.445 (6H, s, SCH$_3$). $^{31}$P NMR ($^1$H dec., 121 MHz, D$_2$O), ppm: 2.30-1.72 (m, P$^2$+P$^3$), −10.55-−11.05 (m, P$^1$+P$^4$). Electrospray MS in the negative ionization mode: Observed, m/z, 959.2 (100.0%), 960.2 (33.1%), 961.1 (50.5%), 962.1 (13.5%), 963.1 (6.6%), 964.1 (1.4%); Calculated for [M-H]$^-$, C$_{23}$H$_{32}$ClN$_{10}$O$_{18}$P$_4$S$_2$—, m/e: 959.0 (100.0%), 960.0 (31.2%), 961.0 (49.4%), 962.0 (14.3%), 963.0 (6.8%), 964.0 (1.6%).

Example 4

Synthesis of Compound 17, P$^1$,P$^4$-bis-(2-methylthio-5'-adenosine)-P$^1$,P$^4$-dithio-P$^2$, P$^3$-monochloromethylenetetraphosphate Compound 17 was prepared by the method in Example 1, steps e, and f, as the tetrasodium salt in 81% yield from 2-methylthioadenosine-5'-thiomonophosphate as the bis-triethylammonium salt, which was prepared as per Example 2, and disodium chloromethylenebis-(1-imidazolylphosphinic acid), which was prepared as per Example 3. This compound is a mixture of 4 diastereomers with different stereo-configuration at P$^1$, P$^4$, and the carbon atom between P$^2$ and P$^3$. When P$^1$ and P$^4$ are in the same absolute configuration, namely R$_{P1}$R$_{P4}$ or S$_{P1}$ S$_{P4}$, the carbon atom between P$^2$ and P$^3$ has two equivalent substituents, is pro-chiral, and therefore does not contribute to formation of additional stereo-isomers. When P$^1$, and P$^4$ are in different absolute configuration, namely S$_{P1}$R$_{P4}$ or R$_{P1}$ S$_{P4}$, the carbon atom between P$^2$ and P$^3$ has two different substituents, becomes chiral, and contributes to the formation of two additional stereo-isomers. Therefore the configuration of the four observed stereo-isomers is: R$_{P1}$, R$_{P4}$; S$_{P1}$, S$_{P4}$; R$_{P1}$, R$_C$, S$_{P4}$, which is equivalent to S$_{P1}$, R$_C$, R$_{P4}$ and therefore is a meso form; and R$_{P1}$, S$_C$, S$_{P4}$, which is equivalent to S$_{P1}$, S$_c$, R$_{P4}$, and represents another meso form. Here R$_C$, or S$_c$ represents the absolute stereo-configuration of the carbon atom between P$^2$ and P$^3$. The four individual diastereomers can be separated by analytical and preparative reverse phase HPLC as described in Example 2. The characterization of compound 17 is as follows: $^1$H NMR (300 MHz, D$_2$O) δ 8.35-8.11 (multiple s, 2H, H-8), 6.09-5.94 (m, 2H, H-1'), 4.90-4.35 (1H, multiple t, CH—Cl), 4.82-4.70 (m, 2H, H-2'), 4.60-4.50 (m, 2H, H-3'), $\overline{4.37}$-4.13 (m, 6H, H-4'+H'5'), 2.53-2.47 (ms, 6H, SCH$_3$). $^{31}$P NMR ($^1$H dec., 121 MHz, D$_2$O), ppm: 43.15-42.02 (m, P$^1$+P$^4$), 2.00-1.22 (m, P$^2$+P$^3$). Electrospray MS in the negative ionization mode: Observed, m/z, 990.9 (100.0%), 991.9 (29.5%) 992.9 (56.7%), 993.9 (16.6%), 994.8, (10.0%); Calculated for [M-H]$^-$, C$_{23}$H$_{32}$ClN$_{10}$O$_{16}$P$_4$S$_4$, m/e: 990.95 (100.0%), 991.96 (32.8%), 992.95 (57.5%), 993.95 (17.1%), 994.94 (11.5%).

Example 5

Synthesis of Compound 23, P$^1$,P$^4$-bis-(2-ethylthio-5'-adenosine)-P$^1$,P$^4$-dithio-P$^2$,P$^3$-monochloromethylenetetraphosphate Compound 23 was made by the methods described in Examples 1-4 as the tetrasodium salt in 56% yield from 2-ethylthioadenosine-5'-thiomonophosphate as the bis-triethylammonium salt and disodium chloromethylenebis-(1-imidazolylphosphinic acid). 2-Ethylthioadenosine-5'-thiomonophosphate was prepared as per Example 2 from 2-ethylthioadenosine, which was prepared by reaction of 2-thioadenosine with ethyl iodide using the method for synthesis of 2-methylthioadenosine described in Example 1. Compound 23 was prepared as a mixture of 4 diastereomers with different stereo-configuration at P$^1$, and P$^4$, and the carbon atom between P$^2$ and P$^3$, and which absolute configuration is analogous to the absolute configuration of the stereo-isomers of compound 17 described in Example 4.

Compound 23: $^1$H NMR (300 MHz, D$_2$O) δ 8.15-8.02 (multiple s, 2H, H-8), 5.88-5.83 (m, 2H, H-1'), 4.78-4.35 (1H, multiple t, CH—Cl), 4.67-4.55 (m, 2H, H-2'), 4.42-4.35 (m, 2H, H-3'), 4.$\overline{22}$-4.13 (m, 2H, H-4'), 4.13-3.98 (m, 4H, H-5'), 3.00-2.86 (m, 4H, SCH$_2$), 1.21-1.12 (mt, 6H, CH$_3$). $^{31}$P NMR ($^1$H dec., 121 MHz, D$_2$O), ppm: 44.32-42.78 (m, P$^1$+P$^4$), 2.79-2.12 (m, P$^2$+P$^3$). Electrospray MS in the negative ionization mode: Observed, m/z, 1019.1 (100%), 1020.1 (38.0%), 1021.0 (53.8%), 1022.0 (19.5%), 1022.9 (11.8%), 1023.9 (3.1%); Calculated for [M-H]$^-$, C$_{25}$H$_{36}$ClN$_{10}$O$_{16}$P$_4$S$_4$–, m/e: 1018.98 (100.0%), 1019.99 (33.0%), 1020.98 (59.3%), 1021.98 (19.1%), 1022.98 (12.0%), 1023.98 (2.3%).

Example 6

Synthesis of Compound 32, P$^1$,P$^4$-bis(2-propylthio-5'-adenosine)-P$^1$,P$^4$-dithio-P$^2$,P$^3$-monochloromethylenetetraphosphate Compound 32 was prepared by the methods described in Examples 1-4 as the tetrasodium salt in 70% yield from 2-propylthioadenosine-5'-thiomonophosphate as the bis-triethylammonium salt and disodium chloromethylenebis-(1-imidazolylphosphinic acid). 2-Propylthioadenosine-5'-thiomonophosphate was prepared as per Example 2 from 2-propylthioadenosine, which was prepared by reaction of 2-thioadenosine with propyl iodide using the method for synthesis of 2-methylthioadenosine described in Example 1. Compound 32 is a mixture of 4 diastereomers with different stereo-configuration at P$^1$, P$^4$, and the carbon atom between P$^2$ and P$^3$, and which absolute configuration is analogous to the absolute configuration of the stereo-isomers of compound 17 described in Example 4.

Compound 32: $^1$H NMR (300 MHz, D$_2$O) δ 8.29-7.95 (multiple s, 2H, H-8), 5.89-5.82 (m, 2H, H-1'), 4.81-4.31 (1H, multiple t, CH—Cl), 4.67-4.55 (m, 2H, H-2'), 4.43-4.33 (m, 2H, H-3'), 4.$\overline{24}$-4.16 (m, 2H, H-4'), 4.16-4.00 (m, 4H, H-5'), 2.98-2.81 (m, 4H, SCH$_2$), 1.63-1.42 (m, 4H, SCH$_2$CH$_2$), 0.87-0.78 (multiple t, 6H, CH$_3$). $^{31}$P NMR ($^1$H dec., $\overline{121}$ MHz, D$_2$O), ppm: 43.8-42.5 (m, P$^1$+P$^4$), 3.1-1.8 (m, P$^2$+P$^3$). Electrospray MS in the negative ionization mode: Observed, m/z, 1047.0 (100%), 1048.0 (36.7%), 1048.9 (55.3%), 1049.9, (18.4%), 1050.9, (10.8%), 1051.9 (4.6%); Calculated for [M-H]⁻, $C_{27}H_{40}ClN_{10}O_{16}P_4S_4$—, m/e: 1047.0 (100.0%), 1048.0 (37.2%), 1049.0 (60.0%), 1050.0 (20.5%), 1051.0 (12.4%), 1052.0 (3.6%).

Example 7

Synthesis of Compound 34, $P^1,P^4$-bis(2-(3,3,3,-trifluoropropylthio)-5'-adenosine)-$P^1,P^4$-dithio-$P^2,P^3$-monochloromethylenetetraphosphate Compound 34 was made by the methods described in Examples 1-4 as the tetrasodium salt in 61% yield from 2-(3,3,3-trifluoropropylthio)adenosine-5'-thiomonophosphate as the bis-triethylammonium salt and disodium chloromethylenebis-(1-imidazolylphosphinic acid). 2-(3,3,3-Trifluoropropylthio)adenosine-5'-thiomonophosphate was prepared as per Example 2 from 2-(3,3,3-trifluoropropylthio) adenosine, which was prepared by reaction of 2-thioadenosine with 1-iodo-3,3,3-trifluoropropane using the method for synthesis of 2-methylthioadenosine described in Example 1. Compound 34 was isolated as a mixture of 4 diastereomers with different stereo-configuration at $P^1$, $P^4$, and the carbon atom between $P^2$ and $P^3$, and which absolute configuration is analogous to the absolute configuration of the stereo-isomers of compound 17 described in Example 4.

Compound 34: ¹H NMR (300 MHz, D₂O) δ 8.27-8.11 (multiple s, 2H, H-8), 5.98-5.92 (m, 2H, H-1'), 4.94-4.41 (1H, multiple t, CH—Cl), 4.69-4.61 (m, 2H, H-2'), 4.53-4.44 (m, 2H, H-3'), 4.$\overline{32}$-4.25 (m, 2H, H-4'), 4.25-4.12 (m, 4H, H-5'), 3.23-3.13 (m, 4H, SCH₂), 2.70-2.50 (m, 4H, CH₂CF₃). ³¹P NMR (¹H dec., 121 MHz, D₂O), ppm: 44.1-42.7 (m, P¹+P⁴), 2.98-2.15 (m, P²+P³). Electrospray MS in the negative ionization mode: Observed, m/z, 1155.1 (100%), 1156.16 (35.8%), 1157.0 (55.3%), 1158.0 (18.6%), 1159.0 (10.3%), 1160.0 (3. %); Calculated for [M-H]⁻, $C_{27}H_{34}ClF_6N_{10}O_{16}P_4S_4$—, m/e: 1155.0 (100.0%), 1156.0 (37.1%), 1157.0 (60.0%), 1158.0 (20.4%), 1159.0 (11.1%), 1160.0 (3.3%).

Example 8

Synthesis of Compound 37, $P^1,P^4$-bis-(2-pentylthio-5'-adenosine)-$P^1,P^4$-dithio-$P^2,P^3$-monochloromethylenetetraphosphate Compound 37 was made by the methods described in Examples 1-4 as the tetrasodium salt in 64% yield from 2-pentylthioadenosine-5'-thiomonophosphate as the bis-triethylammonium salt and disodium chloromethylenebis-(1-imidazolylphosphinic acid). 2-Pentylthioadenosine-5'-thiomonophosphate was prepared as per Example 2 from 2-pentylthioadenosine, which was prepared by reaction of 2-thioadenosine with n-pentyl iodide using the method for synthesis of 2-methylthioadenosine described in Example 1. Compound 37 was isolated as a mixture of 4 diastereomers with different stereo-configuration at $P^1$, $P^4$, and the carbon atom between $P^2$ and $P^3$, and which absolute configuration is analogous to the absolute configuration of the stereo-isomers of compound 17 described in Example 4.

Compound 37: ¹H NMR (300 MHz, D₂O) δ 8.26-8.12 (multiple s, 2H, H-8), 5.98-5.93 (m, 2H, H-1'), 4.89-4.39 (1H, multiple t, CH—Cl), 4.73-4.64 (m, 2H, H-2'), 4.52-4.45 (m, 2H, H-3'), 4.$\overline{32}$-4.23 (m, 2H, H-4'), 4.23-4.11 (m, 4H, H-5'), 3.03-2.92 (m, 4H, SCH₂), 1.63-1.50 (m, 4H, SCH₂CH₂), 1.34-1.12 (m, 8H, CH₂CH₂CH₃), 0.82-0.72 (m, 6H, $\overline{CH_3}$). ³¹P NMR (¹H dec., $\overline{121\text{ MHz}}$, D₂O), ppm: 44.05-42.83 (m, P¹+P⁴), 2.96-2.13 (m, P²+P³). Electrospray MS in the negative ionization mode: Observed, m/z, 1103.3 (100%), 1104.3 (43.1%), 1105.1 (61.8%), 1106.1 (21.8%), 1107.0 (11.0%), 1108.0 (3.2%); Calculated for [M-H]⁻, $C_{31}H_{48}ClN_{10}O_{16}P_4S_4$—, m/e: 1103.1 (100.0%), 1104.1 (41.6%), 1105.1 (61.8%), 1106.1 (23.1%), 1107.1 (13.3%), 1108.1 (4.1%).

Example 9

Synthesis of Compound 44, $P^1,P^4$-bis(2-chloro-5'-adenosine)-$P^1,P^4$-dithio-$P^2,P^3$-monochloromethylenetetraphosphate Compound 44 was made by the methods described in Examples 1-4 as the tetrasodium salt in 69% yield from 2-chloroadenosine-5'-thiomonophosphate as the bis-triethylammonium salt, and disodium chloromethylenebis-(1-imidazolylphosphinic acid). 2-Chloroadenosine-5'-thiomonophosphate was prepared as per Example 2 from 2-chloroadenosine (Sigma-Aldrich, St. Louis, Mo.). Compound 44 was isolated as a mixture of 4 diastereomers with different stereo-configuration at $P^1$, $P^4$, and the carbon atom between $P^2$ and $P^3$, and which absolute configuration is analogous to the absolute configuration of the stereo-isomers of compound 17 described in Example 4.

Compound 44: ¹H NMR (300 MHz, D₂O) δ 8.39-8.26 (multiple s, 2H, H-8), 5.91-5.86 (m, 2H, H-1'), 4.90-4.39 (1H, multiple t, CH—Cl), 4.70-4.61 (m, 2H, H-2'), 4.53-4.46 (m, 2H, H-3'), 4.$\overline{36}$-4.27 (m, 2H, H-4'), 4.27-4.11 (m, 4H, H-5'). ³¹P NMR (¹H dec., 121 MHz, D₂O), ppm: 43.75-42.42 (m, P¹+P⁴), 2.63-1.95 (m, P²+P³). Electrospray MS in the negative ionization mode: Observed, m/z, 967.0 (92.2%), 968.0 (27.0%), 969.0 (100.0%), 970.0 (28.9%), 971.0 (42.0%), 972.0 (10.3%), 973.0 (8.6%), 973.9 (1.8%); Calculated for [M-H]⁻, $C_{21}H_{26}Cl_3N_{10}O_{16}P4S_2$—, m/e: 966.9 (89.1%), 967.9 (25.8%), 968.9 (100.0%), 969.9 (28.1%), 970.9 (42.3%), 971.9 (11.4%), 972.9 (8.3%), 973.9 (2.1%).

Example 10

Synthesis of Compound 40, $P^1,P^1$-bis-(2-iodo-5'-adenosine)-$P^1,P^4$-dithio-$P^2$, $P^3$-monochloromethylenetetraphosphate Compound 40 was prepared by the methods in Examples 1-4 as the tetrasodium salt in 73% yield from 2-iodoadenosine-5'-thiomonophosphate as the bis-triethylammonium salt, and disodium chloromethylenebis-(1-imidazolylphosphinic acid). 2-Iodoadenosine-5'-thiomonophosphate was prepared as per Example 2 from 2-iodoadenosine (Sigma-Aldrich, St. Louis, Mo.). Compound 40 was isolated as a mixture of 4 diastereomers with different stereo-configuration at $P^1$, $P^4$, and the carbon atom between $P^2$ and $P^3$, and which absolute configuration is analogous to the absolute configuration of the stereo-isomers of compound 17 described in Example 4.

Compound 40: ¹H NMR (300 MHz, D₂O) δ 8.38-8.16 (multiple s, 2H, H-8), 5.89-5.84 (m, 2H, H-1'), 4.93-4.39 (1H, multiple t, CH—Cl), 4.64-4.57 (m, 2H, H-2'), 4.52-4.45 (m, 2H, H-3'), 4.$\overline{34}$-4.27 (m, 2H, H-4'), 4.27-4.14 (m, 4H, H-5'). ³¹P NMR (¹H dec., 121 MHz, D₂O), ppm: 43.95-42.45 (m, P¹+P⁴), 3.13-2.02 (m, P²+P³). Electrospray MS in the negative ionization mode: Observed, m/z, 1151.0 (100.0%), 1152.0 (29.7%), 1152.9 (46.2%), 1153.9 (13.7%), 1154.9 (5.8%), 1155.9 (1.3, %); Calculated for [M-H]⁻, $C_{21}H_{26}ClN_{10}O_{16}P_4S_2^-$, m/e: 1150.8 (100.0%), 1151.8 (28.9%), 1152.8 (48.3%), 1153.8 (13.1%), 1154.8 (6.3%), 1155.8 (1.4%).

Example 11

Synthesis of Compound 22, $P^1,P^4$-bis($N^6$-methyl-2-methylthio-5'-adenosine)-$P^1,P^4$-dithio-$P^2,P^3$-monochloromethylenetetraphosphate Compound 22 was prepared by the methods in Examples 1-4 as the tetrasodium salt in 72% yield from $N^6$-methyl-2-methylthioadenosine-5'-thiomonophosphate and disodium chloromethylenebis-(1-imidazolylphosphinic acid). $N^6$-Methyl-2-methylthioadenosine-5'-thiomonophosphate was prepared as per Example 2 from $N^6$-methyl-2-methylthioadenosine. $N^6$-Methyl-2-methylthioadenosine was prepared from 2-methylthioadenosine using the method of Ingall et al. (J. Med. Chem. 1999 42:213-220), according to the scheme:

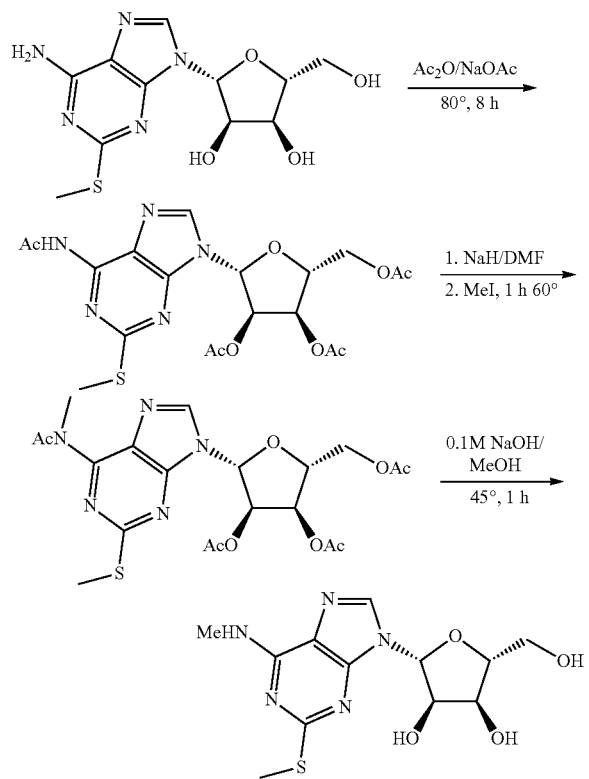

Compound 22 was isolated as a mixture of 4 diastereomers with different stereo-configuration at $P^1$, $P^4$, and the carbon atom between $P^2$ and $P^3$, and which absolute configuration is analogous to the absolute configuration of the stereo-isomers of compound 17 described in Example 4.

Compound 40: $^1$H NMR (300 MHz, $D_2O$) δ 8.10-7.90 (2H, ms, H-8), 5.90-5.83 (2H, md, H-1'), 5.03-4.35 (1H, mt, C H—Cl), 4.75-4.63 (2H, m, H-2'), 4.52-4.43 (2H, m, H-3'), $\overline{4}$.29-4.21 (2H, m, H-4'), 4.21-4.02 (4H, m, H-5'), 2.88-2.71 (6H, ms, $SCH_3$), 2.40-2.25 (6H, ms, $NCH_3$). $^{31}$P NMR ($^1$H dec., 121 MHz, $D_2O$), ppm: 41.96-40.32 (m, $P^1$-$P^4$), 0.69-- 0.16 (m, $P^2$+$P^3$). Electrospray MS in the negative ionization mode: Observed, 1019.0 (100.0%), 1020.0 (36.6%), 1020.9 (53.8%), 1021.9 (18.0%), 1022.9 (11.3%); Calculated for [M-H]$^-$, $C_{25}H_{36}ClN_{10}O_{16}P_4S_4^-$: 1019.0 (100.0%), 1020.0 (35.0%), 1021.0 (59.3%), 1022.0 (19.2%), 1023.0 (12.0%)

Example 12

Synthesis of Compound 12, $P^1,P^4$-bis($N^6$-propyl-5'-adenosine)-$P^1,P^4$-dithio-$P^2,P^3$-monochloromethyl-enetetraphosphate Compound 12 was made by the methods described in Examples 1-4 as the tetrasodium salt in 69% yield from $N^6$-propyladenosine-5'-thiomonophosphate as the bis-tri-ethylammonium salt, and disodium chloromethylenebis-(1-imidazolylphosphinic acid). $N^6$-Propyladenosine-5'-thiomonophosphate was prepared as per Example 2 from $N^6$-propyladenosine. $N^6$-propyladenosine was prepared from inosine and n-propylamine according to the method of Wan et al. (Org. Lett., 2005, 7:5877-5880). Compound 12 was isolated as a mixture of 4 diastereomers with different stereo-configuration at $P^1$, $P^4$, and the carbon atom between $P^2$ and $P^3$, and which absolute configuration is analogous to the absolute configuration of the stereo-isomers of compound 17 given in Example 4.

Compound 12: $^1$H NMR (300 MHz, $D_2O$) δ 8.38-8.19 (2H, multiple s, H-8), 7.95-7.90 (multiple s, 2H, H-2), 5.98-5.91 (2H, m, H-1'), 4.98-4.42 (1H, multiple t, CH—Cl), 4.77-4.64 (2H, m, H-2'), 4.55-4.47 (2H, m, H-3'), $\overline{4}$.36-4.27 (2H, m, H-4'), 4.27-4.09 (4H, m, H-5'), 3.30-3.11 (4H, multiple b s, $NCH_2$), 1.61-1.46 (m, 4H, $NCH_2CH_2$), 0.92-0.83 (m, 6H, $CH_3$). $^{31}$P NMR ($^1$H dec., 121 MHz, $D_2O$), ppm: 44.02-42.41 (m, $P^1$+$P^4$), 2.97-2.03 (m, $P^2$+$P^3$). Electrospray MS in the negative ionization mode: Observed, 983.1 (100.0%), 984.1 (33.6%), 985.1 (48.3%), 986.1 (15.0%), 987.0 (6.9%), 988.1 (1.5%); Calculated for [M-H]$^-$, $C_{27}H_{40}ClN_{10}O_{16}P_4S_2^-$, m/e: 983.1 (100.0%), 984.1 (35.6%), 985.1 (50.4%), 986.1 (16.4%), 987.1 (7.3%), 988.1 (1.9%)

Example 13

Synthesis of Compound 8, $P^1,P^4$-bis($N^6$-methyl-5'-adenosine)-$P^1,P^4$-dithio-$P^2,P^3$-monochloromethyl-enetetraphosphate Compound 8 was prepared following Example 12, using methylamine, instead of n-propylamine. The product was isolated as the tetrasodium salt in 66% yield, and consisted of 4 diastereomers with different stereo-configuration at $P^1$, $P^4$, and the carbon atom between $P^2$ and $P^3$, and which absolute configuration is analogous to the absolute configuration of the stereo-isomers of compound 17 given in Example 4.

Compound 8: $^1$H NMR (300 MHz, $D_2O$) δ 8.38-8.16 (2H, ms, H-8), 7.98-7.92 (ms, 2H, H-2), 5.98-5.91 (2H, m, H-1'), 5.03-4.42 (1H, mt, CH—Cl), 4.77-4.68 (2H, m, H-2'), 4.55-4.47 (2H, m, H-3'), $\overline{4}$.37-4.29 (2H, m, H-4'), 4.29-4.08 (4H, m, H-5'), 2.90-2.82 (6H, ms, $NCH_3$). $^{31}$P NMR ($^1$H dec., 121 MHz, $D_2O$), ppm: 43.97-42.43 (m, $P^{1'}$+$P^4$), 3.03-1.92 (m, $P^2$+$P^3$). Electrospray MS in the negative ionization mode: Observed, 927.1 (100.0%), 928.1 (31.9%), 929.1 (47.0%), 930.1 (19.3%), 931.0 (8.1%); Calculated for [M-H]$^-$, $C_{23}H_{32}ClN_{10}O_{16}P_4S_2^-$, m/e: 927.0 (100.0%), 929.0 (49.0%), 928.0 (31.1%), 930.0 (14.2%), 931.0 (6.6%).

Antiplatelet Activity

Platelet aggregation was initiated by adding ADP (3 μM) in the presence or absence of various concentrations of test compound to platelet-rich human plasma, and the aggregation response was recorded for six minutes in a Chrono-log® aggregometer running the Aggro/Link software (Chrono-log®, Havertown, Pa.).

Potency of example compounds to inhibit platelet aggregation is shown in Table 2.

TABLE 2

Platelet inhibition.

| Example | Substituents | | | | | Platelet inhibition |
| | $R_2/R_2'$ | $R_6/R_6'$ | X | X' | Y | $IC_{50}{}^a$ |
| --- | --- | --- | --- | --- | --- | --- |
| (Ap$_4$A) | H | H | O | O | O | 9.8 ± 2.8 |
| (diS-Ap$_4$A) | H | H | S | S | O | 3.3 ± 1.2 |
| 2 | SMe | H | O | O | O | 0.089 ± 0.038 |
| 10 | SMe | H | S | S | O | 0.05 ± 0.037 |
| 17 | SMe | H | S | S | CHCl | 0.013 ± 0.010 |
| 32 | SPr | H | S | S | CHCl | 0.015 ± 0.010 |
| 44 | Cl | H | S | S | CHCl | 0.098 ± 0.004 |
| 40 | I | H | S | S | CHCl | 0.021 ± 0.006 |
| 8 | H | Me | S | S | CHCl | 3.52 ± 0.83 |
| 12 | H | Pr | S | S | CHCl | 5.56 ± 1.7 |
| 22 | SMe | Me | S | S | CHCl | 0.26(n = 1) |

$^a$IC$_{50}$ (average of 2 experiments) in μM for inhibition of 3 μM ADP-induced human platelet aggregation measured by optical aggregometry.

Antithrombotic Activity In Vivo

The methods of Sturgeon et al. (J. Pharm. Toxicol. Meth. 53:20-29, 2006) are used to test the antithrombotic activity of compounds in mice, rats, and rabbits. The method of Folts (Circulation 83 (Suppl IV):3-14, 1991) is used to test the antithrombotic activity of compounds in dogs.

Other Embodiments

All publications, patent applications, patents, and other documents cited herein are incorporated by reference in their entirety. In case of conflict, the present specification, including definitions, will control. In addition, the materials, methods, and examples are illustrative only and not intended to be limiting.

Other variations and embodiments of the invention described herein will now be apparent to those of ordinary skill in art without departing from the scope of the invention or the spirit of the claims below.

Other embodiments are in the claims.

What is claimed is:

1. A compound of formula I

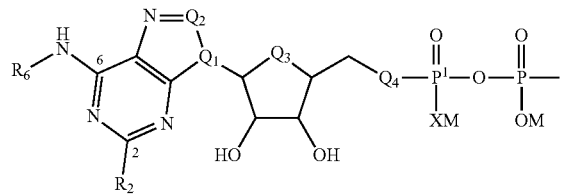

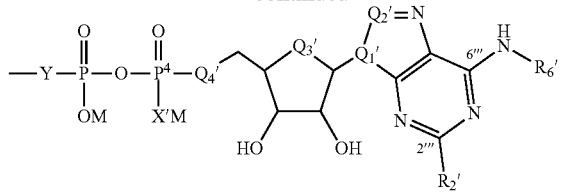

-continued where $R_2$ and $R_2'$ are, independently, —H, —F, —Cl, —Br, —I, —R, —OR, —SR, —NHR, —OCOR, —SCOR, or —NHCOR;

$R_6$ and $R_6'$ are, independently, —H, —R, or —COR, provided that $R_2$ and $R_6$ and $R_2'$ and $R_6'$ are not simultaneously H;

$Q_1$, $Q_2$, $Q_1'$, and $Q_2'$ are independently N or CH;

$Q_3$, $Q_4$, $Q_3'$, and $Q_4'$ are independently O or CH$_2$;

X and X' are, independently, O or S;

Y is O or CZZ', where Z and Z' are, independently, —H, —F, —Cl, —Br, —R, —OR, —SR, —NHR, —OCOR, —SCOR or —NHCOR;

R is straight or branched chain alkyl (C1-C6), cyclic alkyl (C3-C6), straight or branched chain alkenyl (C2-C6), cyclic alkenyl (C4-C6), straight or branched chain alkynyl (C2-C6), cyclic alkynyl (C8-C10), aryl (C6-C12), heteroaryl (C2-C9), or heterocyclyl (C2-C9), wherein the alkyl, cyclic alkyl, alkenyl, cyclic alkenyl, alkynyl, cyclic alkynyl, aryl, heteroaryl, and heterocyclyl groups are substituted or unsubstituted; and each M is independently H or a pharmaceutically acceptable cation, wherein when two or more M are pharmaceutically acceptable cations, they may be combined to form a single pharmaceutically acceptable cation with the appropriate charge; or a pharmaceutically acceptable salt thereof or stereoisomer thereof.

2. The compound of claim 1, having the formula:

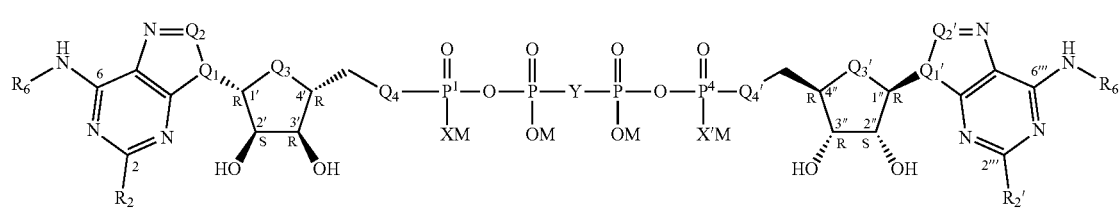

Formula Ia or a pharmaceutically acceptable salt thereof or stereoisomer thereof.

3. The compound of claim 1, having the formula:

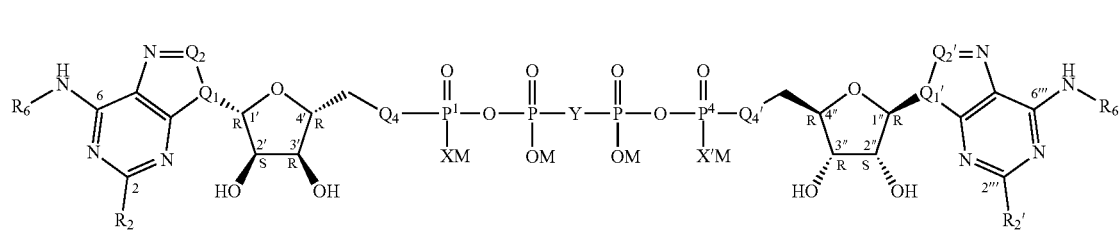

Formula II or a pharmaceutically acceptable salt thereof or stereoisomer thereof.

4. The compound of claim 1, having the formula:

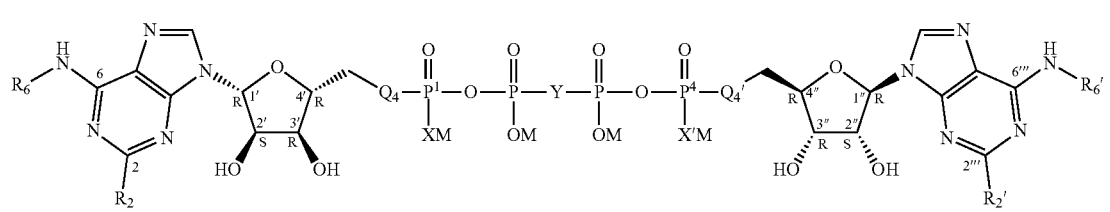

Formula III or a pharmaceutically acceptable salt thereof or stereoisomer thereof.

5. The compound of claim 1, wherein $R_2$ and $R_2'$ are, independently, —H, —F, —Cl, —Br, —I, —OR, —SR, —NHR, —OCOR, —SCOR, or —NHCOR, in which R is straight or branched chain alkyl (C1-C6), polyfluoroalkyl, or substituted alkyl (C2-C6);

$R_6$ and $R_6'$ are, independently, —H, —R, or —COR, in which R is straight or branched chain alkyl (C1-C6), polyfluoroalkyl, or substituted alkyl (C2-C6);

Y is O or CZZ', where Z and Z' are, independently, —H, —F, —Cl, —Br, —R, —OR, —SR, —NHR, —OCOR, —SCOR, or —NHCOR, where R is straight or branched chain alkyl (C1-C6), polyfluoroalkyl, or substituted alkyl (C2-C6);

$Q_1$ and $Q_1'$ are N;
$Q_2$ and $Q_2'$ are CH; and
$Q_3$, $Q_4$, $Q_3'$, and $Q_4'$ are O.

6. The compound of claim 1, wherein X and X' are S, and Y is $CH_2$, CHCl, $CCl_2$, CHF, or $CF_2$.

7. The compound of claim 6, wherein $R_6$ is H, and $R_2$ is RS, where R is straight or branched chain alkyl (C1-C6), which is unsubstituted or substituted with one or more halogen atoms, aryl groups, heteroaryl groups, heterocyclyl groups, oxo groups, hydroxyl groups, alkoxy groups, aryloxy groups, alkylthio groups, arylthio groups, alkylamino groups, or aryl amino groups.

8. The compound of claim 6, wherein $P^1$ is in the S or R configuration, and $P^4$ is in the same configuration.

9. The compound of claim 6, wherein $P^1$ is in the S or R configuration, and $P^4$ is in the opposite configuration.

10. The compound of claim 1, wherein X and X' are S, and Y is O.

11. The compound of claim 10, wherein $R_6$ is H, and $R_2$ is RS, where R is straight or branched chain alkyl (C1-C6), which is unsubstituted or substituted with one or more halogen atoms, aryl groups, heteroaryl groups, heterocyclyl groups, oxo groups, hydroxyl groups, alkoxy groups, aryloxy groups, alkylthio groups, arylthio groups, alkylamino groups, or aryl amino groups.

12. The compound of claim 10, wherein P' is in the S or R configuration, and $P^4$ is in the same configuration.

13. The compound in claim 10, wherein $P^1$ is in the S or R configuration, and $P^4$ is in the opposite configuration.

14. A compound of claim 1, selected from the following table:

| Cpd No. | $R_2$ | $R_6$ | $R_2'$ | $R_6'$ | X | Y | X' | $Q_1$ and $Q_1'$ | $Q_2$ and $Q_2'$ | $Q_3$ and $Q_3'$ | $Q_4$ and $Q_4'$ | $P^1$ Config | $P^4$ Config |
|---|---|---|---|---|---|---|---|---|---|---|---|---|---|
| 1 | H | Me | H | Me | O | O | O | N | CH | O | O | R/S | R/S |
| 2 | SMe | H | SMe | H | O | O | O | N | CH | O | O | R/S | R/S |
| 3 | SMe | Me | H | H | O | O | O | N | CH | O | O | R/S | R/S |
| 4 | SMe | H | H | H | O | O | O | N | CH | O | O | R/S | R/S |
| 5 | SMe | H | H | Me | O | O | O | N | CH | O | O | R/S | R/S |
| 6 | SMe | Me | SMe | H | O | O | O | N | CH | O | O | R/S | R/S |
| 7 | SMe | Me | SMe | Me | O | O | O | N | CH | O | O | R/S | R/S |
| 8 | H | Me | H | Me | S | CHCl | S | N | CH | O | O | R/S | R/S |
| 9 | SMe | H | SMe | H | O | CHCl | O | N | CH | O | O | R/S | R/S |
| 10 | SMe | H | SMe | H | S | O | S | N | CH | O | O | R/S | R/S |
| 11 | SMe | Me | H | H | S | O | S | N | CH | O | O | R/S | R/S |
| 12 | H | Pr | H | Pr | S | CHCl | S | N | CH | O | O | R/S | R/S |
| 13 | SMe | H | H | Me | S | O | S | N | CH | O | O | R/S | R/S |
| 14 | SMe | Me | SMe | H | S | O | S | N | CH | O | O | R/S | R/S |
| 15 | SMe | Me | SMe | Me | S | O | S | N | CH | O | O | R/S | R/S |
| 16 | H | Me | H | Me | S | CHCl | S | N | CH | O | O | R/S | R/S |
| 17 | SMe | H | SMe | H | S | CHCl | S | N | CH | O | O | R/S | R/S |
| 18 | SMe | Me | H | H | S | CHCl | S | N | CH | O | O | R/S | R/S |
| 19 | SMe | H | H | H | S | CHCl | S | N | CH | O | O | R/S | R/S |
| 20 | SMe | H | H | Me | S | CHCl | S | N | CH | O | O | R/S | R/S |
| 21 | SMe | Me | SMe | H | S | CHCl | S | N | CH | O | O | R/S | R/S |
| 22 | SMe | Me | SMe | Me | S | CHCl | S | N | CH | O | O | R/S | R/S |
| 23 | SEt | H | SEt | H | S | CHCl | S | N | CH | O | O | R/S | R/S |
| 24 | SEt | Me | SEt | Me | S | CHCl | S | N | CH | O | O | R/S | R/S |
| 25 | SEt | H | SEt | H | S | $CCl_2$ | S | N | CH | O | O | R/S | R/S |
| 26 | SPr | H | H | H | S | CHCl | S | N | CH | O | O | R/S | R/S |
| 27 | SPr | Me | H | H | S | CHCl | S | N | CH | O | O | R/S | R/S |
| 28 | SPr | H | SMe | H | S | CHCl | S | N | CH | O | O | R/S | R/S |
| 29 | SPr | H | H | Me | S | CHCl | S | N | CH | O | O | R/S | R/S |
| 30 | SPr | Me | SMe | H | S | CHCl | S | N | CH | O | O | R/S | R/S |
| 31 | SPr | Me | SMe | Me | S | CHCl | S | N | CH | O | O | R/S | R/S |
| 32 | SPr | H | SPr | H | S | CHCl | S | N | CH | O | O | R/S | R/S |
| 33 | SPr | Me | SPr | Me | S | CHCl | S | N | CH | O | O | R/S | R/S |
| 34 | $CF_3CH_2CH_2S$ | H | $CF_3CH_2CH_2S$ | H | S | CHCl | S | N | CH | O | O | R/S | R/S |
| 35 | $CF_3CH_2CH_2S$ | Me | $CF_3CH_2CH_2S$ | Me | S | CHCl | S | N | CH | O | O | R/S | R/S |
| 36 | $CF_3CH_2CH_2S$ | H | $CF_3CH_2CH_2S$ | H | S | $CCl_2$ | S | N | CH | O | O | R/S | R/S |
| 37 | $n\text{-}C_5H_{11}S$ | H | $n\text{-}C_5H_{11}S$ | H | S | CHCl | S | N | CH | O | O | R/S | R/S |
| 38 | $n\text{-}C_5H_{11}S$ | Me | $n\text{-}C_5H_{11}S$ | Me | S | CHCl | S | N | CH | O | O | R/S | R/S |
| 39 | $n\text{-}C_5H_{11}S$ | H | $n\text{-}C_5H_{11}S$ | H | S | $CCl_2$ | S | N | CH | O | O | R/S | R/S |
| 40 | I | H | I | H | S | CHCl | S | N | CH | O | O | R/S | R/S |
| 41 | I | H | I | H | S | O | S | N | CH | O | O | R/S | R/S |
| 42 | Br | H | Br | H | S | CHCl | S | N | CH | O | O | R/S | R/S |
| 43 | Br | H | Br | H | S | $CCl_2$ | S | N | CH | O | O | R/S | R/S |
| 44 | Cl | H | Cl | H | S | CHCl | S | N | CH | O | O | R/S | R/S |
| 45 | SMe | H | SMe | H | S | $CCl_2$ | S | N | CH | O | O | R/S | R/S |
| 46 | SMe | H | SMe | H | S | $CCl_2$ | O | N | CH | O | O | R/S | R/S |
| 47 | SMe | H | SMe | H | S | $CCl_2$ | S | CH | CH | O | O | R/S | R/S |
| 48 | SMe | H | SMe | H | S | $CCl_2$ | S | N | CH | CH | O | R/S | R/S |
| 49 | SMe | H | SMe | H | S | $CCl_2$ | S | N | CH | O | CH | R/S | R/S |
| 50 | SMe | H | SMe | H | S | $CCl_2$ | S | N | CH | CH | CH | R/S | R/S |
| 51 | SMe | H | SMe | H | S | $CCl_2$ | S | CH | CH | CH | CH | R/S | R/S |
| 52 | SMe | H | SMe | H | S | $CCl_2$ | S | N | N | O | O | R/S | R/S |
| 53 | SMe | H | SMe | H | S | $CCl_2$ | S | CH | N | O | O | R/S | R/S |
| 54 | SMe | H | SMe | H | S | $CCl_2$ | S | CH | N | CH | O | R/S | R/S |
| 55 | SMe | H | SMe | H | S | $CCl_2$ | S | CH | N | CH | O | R/S | R/S |
| 56 | SMe | H | SMe | H | S | $CCl_2$ | S | CH | N | CH | CH | R/S | R/S |
| 57 | SMe | H | SMe | H | S | $CCl_2$ | S | N | CH | O | O | R | R |
| 58 | SMe | H | SMe | H | S | $CCl_2$ | S | N | CH | O | O | R | S |
| 59 | SMe | H | SMe | H | S | $CCl_2$ | S | N | CH | O | O | S | S. |

15. A pharmaceutical composition comprising a compound of claim 1 and a pharmaceutically acceptable excipient.

16. The pharmaceutical composition of claim 15, wherein said composition is formulated for nasal inhalation.

17. A method of inhibiting ADP-induced aggregation of human platelets in vitro, said method comprising contacting human platelets with a compound of claim 1 in an amount sufficient to inhibit ADP-induced aggregation.

18. The method of claim 17, wherein said human platelets are in blood and blood products during storage.

19. A method of inhibiting aggregation of human platelets in vivo, said method comprising administering an amount of a compound of claim 1 sufficient to inhibit platelet aggregation to a human in need thereof.

20. A method of treating a human disease related to platelet aggregation, said method comprising administering a therapeutically effective amount of a compound of claim 1 to a human in need thereof.

21. The method of claim 20, wherein said disease is selected from the group consisting of venous thrombosis, thrombophlebitis, arterial embolism, coronary and cerebral arterial thrombosis associated with unstable angina, coronary angioplasty, or acute myocardial infarction, unstable angina, myocardial infarction, stroke, transient ischemic event, cerebral embolism, kidney embolism, pulmonary embolism, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, pathological effects of atherosclerosis and arteriosclerosis, chronic or acute states of hyper-aggregability, reocclusion of an artery or vein following fibrinolytic therapy, platelet adhesion associated with extracorporeal circulation, coronary artery disease, peripheral artery disease, and thrombotic complications associated with thrombolytic therapy.

22. A method of treating arterial thrombosis, said method comprising administering a therapeutically effective amount of a compound of claim 1 to a human in need thereof.

23. The method of claim 22, wherein said administering is parenteral.

* * * * *